US011494001B2

United States Patent
Sirois et al.

(10) Patent No.: US 11,494,001 B2
(45) Date of Patent: Nov. 8, 2022

(54) GESTURE DETECTION SYSTEM FOR PERSONAL HEAD WEARABLE DEVICE

(71) Applicant: Wisear, Auxerre (FR)

(72) Inventors: Alain Sirois, Paris (FR); Yacine Achiakh, Auxerre (FR)

(73) Assignee: Wisear, Auxerre (FR)

( * ) Notice: Subject to any disclaimer, the term of this patent is extended or adjusted under 35 U.S.C. 154(b) by 0 days.

(21) Appl. No.: 17/750,071

(22) Filed: May 20, 2022

(65) Prior Publication Data

US 2022/0276723 A1  Sep. 1, 2022

Related U.S. Application Data

(63) Continuation of application No. PCT/IB2021/054334, filed on May 19, 2021.

(30) Foreign Application Priority Data

May 19, 2020 (FR) ...................................... 2005020

(51) Int. Cl.
*G06F 3/01* (2006.01)
*A61B 5/296* (2021.01)
(Continued)

(52) U.S. Cl.
CPC .............. *G06F 3/017* (2013.01); *A61B 5/296* (2021.01); *A61B 5/6817* (2013.01);
(Continued)

(58) Field of Classification Search
CPC .......... G06F 3/017; G06F 3/015; G06F 3/013; A61B 5/296; A61B 5/6817; A61B 5/7271;
(Continued)

(56) References Cited

U.S. PATENT DOCUMENTS 5,692,517 A * 12/1997 Junker ................... A61B 5/375
345/157
7,580,028 B2   8/2009 Jeong et al.
(Continued)

FOREIGN PATENT DOCUMENTS

WO    2013017985 A1    2/2013

OTHER PUBLICATIONS

Anonymous, "Driven Right Leg Circuit", Apr. 12, 2020, one page, retrieved from the Internet:URL:https://en.wikipedia.org/w/index.php?title=Driven_right_leg_circuit&oldid=950544310, retrieved on Aug. 3, 2021.
(Continued)

*Primary Examiner* — Patrick Fernandes
(74) *Attorney, Agent, or Firm* — Daylight Law, P.C.

(57) ABSTRACT

Methods and systems related to the field of gesture detection are disclosed herein. A system for a personal head wearable device includes a first electrode and a second electrode. The first electrode and the second electrode measure a bioelectric signal. The system further includes one or more non-transitory computer readable media storing instructions which, when executed by the system, cause the system to analyze the bioelectric signal to recognize a gesture signal in the bioelectric signal using a stored signature model for the gesture signal, and generate an interface signal upon recognizing the gesture signal in the bioelectric signal. The gesture signal is one of a double jaw clenching signal, a triple jaw clenching signal, and a long jaw clenching signal.

31 Claims, 8 Drawing Sheets

(51) Int. Cl.
    *A61B 5/00* (2006.01)
    *H04R 5/033* (2006.01)
(52) U.S. Cl.
    CPC ............ *A61B 5/7271* (2013.01); *G06F 3/015* (2013.01); *H04R 5/033* (2013.01)
(58) Field of Classification Search
    CPC ... A61B 5/389; A61B 5/4542; A61B 5/02438; A61B 5/24; A61B 5/4547; H04R 5/033
    See application file for complete search history.

(56) References Cited

U.S. PATENT DOCUMENTS

| | | | |
|---|---|---|---|
| 2004/0199084 A1* | 10/2004 | Kelleher | A61B 5/24 600/554 |
| 2006/0215847 A1 | 9/2006 | Hollemans et al. | |
| 2014/0088394 A1* | 3/2014 | Sunderland | A61B 5/6843 600/373 |
| 2015/0126845 A1* | 5/2015 | Jin | G06F 1/163 600/383 |
| 2016/0073914 A1* | 3/2016 | Lapetina | A61B 5/282 600/384 |
| 2018/0074584 A1* | 3/2018 | Rudiger | G06F 1/1694 |
| 2019/0192077 A1 | 6/2019 | Kaiser et al. | |
| 2020/0029882 A1* | 1/2020 | Gong | A61B 5/1118 |

OTHER PUBLICATIONS

International Search Report and Written Opinion dated Oct. 12, 2021 from International Application No. PCT/IB2021/054334, 24 pages.

Partial International Search dated Aug. 18, 2021 from International Application No. PCT/IB2021/054334, 16 pages.

* cited by examiner

GESTURE DETECTION SYSTEM FOR PERSONAL HEAD WEARABLE DEVICE

CROSS REFERENCE TO RELATED APPLICATIONS

The application is a continuation of pending International Patent Application No. PCT/IB2021/054334, filed May 19, 2021, which claims the benefit of and priority to French Patent Application No. 2005020, filed May 19, 2020, both of which are incorporated by reference herein in their entireties for all purposes.

BACKGROUND

Wearable devices are electronic devices that are configured to be worn on a user's body and to perform various functions. Wearable devices can be configured to detect electrical activity in the brain of the user using electrodes. These electrodes can capture different types of electric signals, such as electroencephalogram (EEG or brain signals), electrocardiogram (ECG), electromyography (EMG or muscle signal), and electrooculography (EOG or eye movement signal).

While electrodes can provide robust measurements of bioelectric signal patterns associated with EEG, ECG, EOG and EMG readings, these signals are hard to use as control signals. For instance, wearable device neural interfaces configured to capture a muscle movement may confuse a voluntary muscle movements (a control signal) with an unintentional or involuntary muscle movement when the user is in motion (a false signal or noise). This limits the practical application of neural interfaces to situations where the user is still, which is of limited practical utility.

SUMMARY

Methods and systems related to the field of gesture detection are disclosed herein. The system and methods can be for a personal wearable device, such as a personal head-wearable device. For instance, head wearable devices include smart glasses, earpieces generally, walkie talkie earpieces, headset or earbuds, wireless earbuds, VR/AR headsets, earphones, earplugs, etc. Wearable devices can be configured to detect electrical activity in the brain of the user using electrodes attached to the wearable device and configured to be in contact with a portion of the head of the user when the wearable device is worn. For example, electrodes positioned in earbuds, earpieces or near the ear, and more particularly in the ear canal or concha (also called in-ear electrodes), provide exceptional contact. These electrodes can be installed in audio earbud devices or an earpiece to capture different types of electric signals, such as the EEG, ECG, EMG, and EOG signals mentioned above.

The systems disclosed herein can involve the use of neural interfaces for head-worn wearable devices to perform various hands-free control functions. For example, the system can be trained and used to capture clear control signals via the neural interface. The neural interface can be configured for controlling the operations of the personal wearable device and/or for controlling another device associated with the personal wearable device via those control signals.

To provide a clear control signal independent of a user's motion, bioelectric signals associated to facial muscle movements, such as jaw movements, can be used as control signals. However, the user may involuntarily trigger control signals when speaking, eating, drinking or chewing. Specific embodiments of the invention disclosed herein aim to provide a neural interface for wearable devices that can provide a clear signal in all possible situations for controlling the wearable device or other devices. In this regard, the neural interface can be configured to be activated in response to the detection of a jaw gesture involving a voluntary muscle contraction (e.g., a gesture control by the jaw) consisting of a double jaw clenching, a triple jaw clenching, or a long jaw clenching of the wearer, as these jaw gestures have a very distinct signature compared to a single jaw clench and the other typical jaw movements listed above.

In specific embodiments of the invention, a gesture detection system for a personal head wearable device is provided. The system comprises a first electrode and a second electrode, wherein the first electrode and the second electrode measure a bioelectric signal. The system further comprises one or more computer readable media storing instructions which, when executed by the system, cause the system to analyze the bioelectric signal to recognize a gesture signal in the bioelectric signal using a stored signature model for the gesture signal, and generate an interface signal upon recognizing the gesture signal in the bioelectric signal. The gesture signal is one of a double jaw clenching signal, a triple jaw clenching signal, and a long jaw clenching signal.

In specific embodiments of the invention, a wearable gesture recognition system is provided. The system comprises a first earpiece and a second earpiece. The system further comprises a first electrode and a second electrode, wherein the first electrode and the second electrode are on an exterior surface of the first earpiece, and wherein the first electrode and the second electrode measure a bioelectric signal. The system further comprises a third electrode and a fourth electrode, wherein the third electrode and the fourth electrode are on an exterior surface of the second earpiece, and wherein the third electrode and the fourth electrode measure the bioelectric signal. The system further comprises one or more computer readable media storing instructions which, when executed by the system, cause the system to analyze the bioelectric signal to recognize a gesture signal in the bioelectric signal, and generate an interface signal upon recognizing the gesture signal in the bioelectric signal. The recognizing of the gesture signal in the bioelectric signal uses a combination of data measured by the first electrode and the second electrode, and data measured by the third electrode and the fourth electrode.

In specific embodiments of the invention, a gesture recognition system is provided. The system comprises a first electrode and a second electrode, wherein the first electrode and the second electrode measure a bioelectric signal. The system further comprises a user interface output and one or more computer readable media storing instructions which, when executed by the system, cause the system to generate a prompt to perform a gesture associated with a gesture signal, analyze the bioelectric signal to find the gesture signal in the bioelectric signal using a stored signature for the gesture signal, generate an interface signal upon recognizing the gesture signal in the bioelectric signal, and update the stored signature using the gesture signal to generate a revised stored signature. The interface signal is output on the user interface output. The stored signature is a default signature associated with the gesture.

In specific embodiments of the invention, a gesture detection method for a personal head wearable device is provided. The method comprises measuring a bioelectric signal using a first electrode and a second electrode, wherein the first electrode and the second electrode are located on the personal head wearable device. The method further comprises analyzing the bioelectric signal to recognize a gesture signal in the bioelectric signal using a stored signature model for the gesture signal. The method further comprises generating an interface signal upon recognizing the gesture signal in the bioelectric signal. The gesture signal is one of a double jaw clenching signal, a triple jaw clenching signal, and a long jaw clenching signal.

DETAILED DESCRIPTION

Methods and systems related to the field of gesture detection in accordance with the summary above are disclosed in detail herein. The methods and systems disclosed in this section are nonlimiting embodiments of the invention, are provided for explanatory purposes only, and should not be used to constrict the full scope of the invention.

Specific embodiments of the invention relate to a gesture detection system and method. The system can include neural interfaces (also known as brain computer interfaces or BCI) for wearable devices, such as head-worn wearable devices, to perform various hands-free control functions. In particular, the technology relates to the capture of clear control signals via a neural interface. The neural interface can be configured for controlling the operations of a wearable device and/or for controlling another device, such as controlling a smartphone with earbuds.

The systems in accordance with specific embodiments of the invention can include one or more computer readable media storing instructions which, when executed by the one or more processors of the system, cause the system to perform certain actions or execute method steps. The computer readable media can be non-transitory. The computer readable media can be internal or external to the system. The actions and/or methods steps are described throughout this disclosure as actions/steps that the system is "configured to" perform, in the sense that the system is structural configured to perform those actions/steps (e.g., a processing block of the system can execute instructions to cause the system to behave in a certain way, perform certain actions, and/or provide certain outputs).

Figure 1:
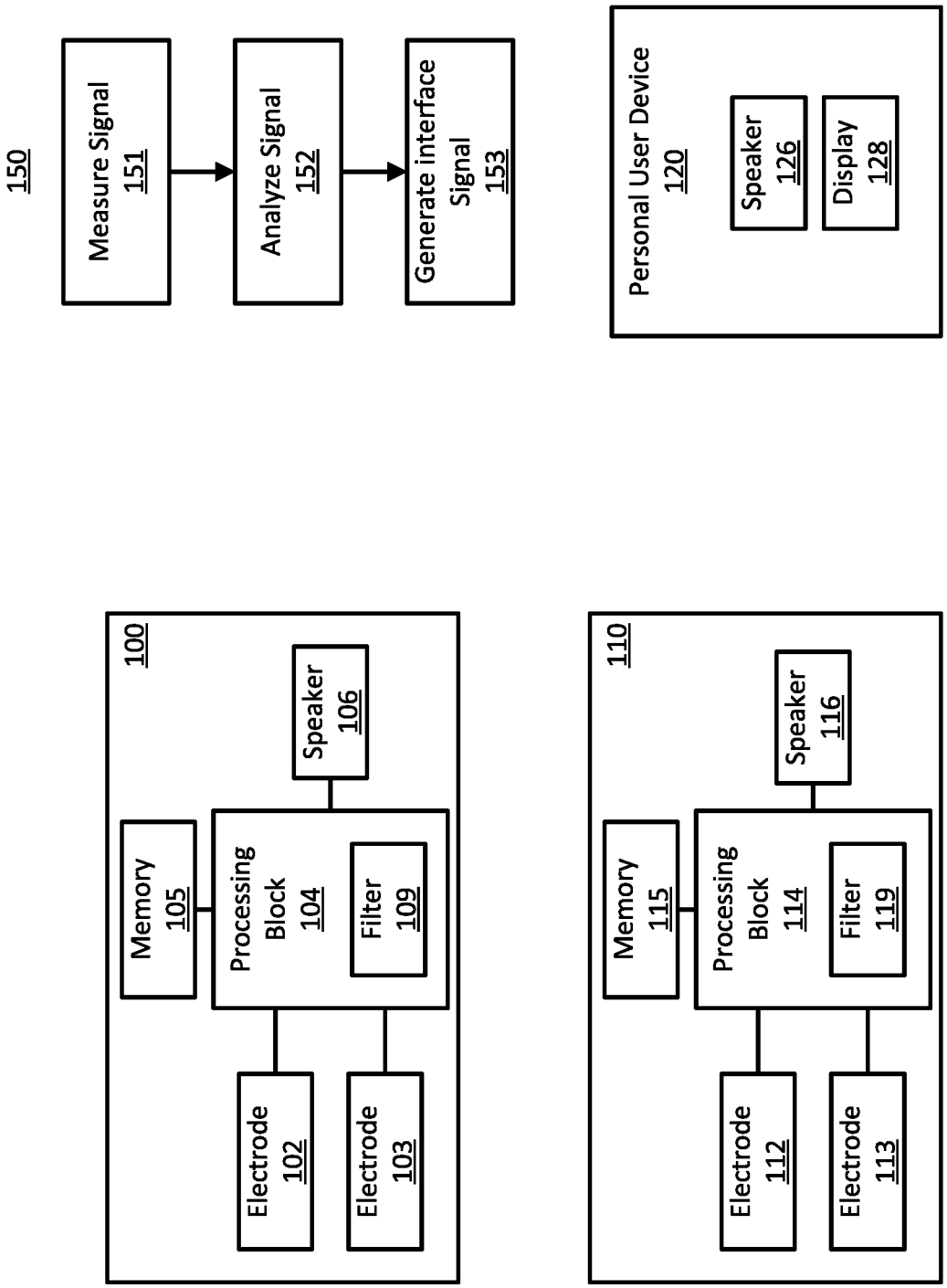
FIG. 1 includes an example of a gesture detection system and a flowchart for a set of methods, in accordance with specific embodiments of the invention disclosed herein.

FIG. 1 includes an example of a gesture detection system 100 and a flowchart 150 for a set of methods in accordance with specific embodiments of the invention disclosed herein. The gesture detection system can be for a wearable device, such as a personal wearable device. A personal wearable device as used in this disclosure is an electronic equipment that performs multimedia activities. Specific embodiments of the invention disclosed herein relate to a wearable device in the form of an earpiece such as an earbud. However, the system of the present invention can be used with any kind of devices, including any kind of wearable devices such as headbands, wristbands, smartwatches, smart rings, belts, etc.

The system in accordance with specific embodiments of the invention can include electrodes, such as electrodes 102 and 103. The electrodes can be placed in contact with the skin of a user, for example when the user wears a personal head wearable device comprising the electrodes. The electrodes can measure a bioelectric signal, as indicated in step 151 of flowchart 150. A bioelectric signal, as used herein, is a physical detectible signal that is generated by the actuation of the nervous system or the internal operation of the brain of a user (e.g., a user who is wearing a wearable device with the electrodes mentioned herein). The term is also used to refer to that same signal as it is electrically sampled, measured, and otherwise analyzed by the gesture detection system. The bioelectric signal can pass along a signal processing path all the way from an analog electrical signal emanating from the brain of the wearer through to digitization and storage in a computer-readable medium as well as additional processing such as the application of digital filtering and other post-digitization processing. The term can refer to a continuous phenomenon or a discrete sampling thereof with the associated definition being apparent from the surrounding context.

Muscle contractions can be triggered by the brain, which sends an electrical signal transmitted along motor neurons, to the muscles considered. When muscle fibers receive the triggering signal transmitted along the motor neurons and contract, they also generate an electrical activity. Electrical activity originating from both the contracting muscles and the motor neurons triggers displacement of surrounding charged particles—ions-, which by their displacement also generate displacement of surrounding ions, creating a cascading effect. This mechanism allows electrical activity generated by muscle contraction and motor neurons to be transmitted across the fluids filling a subject's body, all the way to the skin.

Electrodes consisting of a conductive material, for example metal, can be put in contact with the skin and capture electrical potential changes at the surface of the skin. Those electrodes can be referred to as surface electrodes. This technique is called EMG. This recording technique can use at least two different electrodes (at least one "measurement" electrode, and at least one "reference" electrode). It is possible to have several measurement electrodes, located at different places on the skin.

Figure 2:
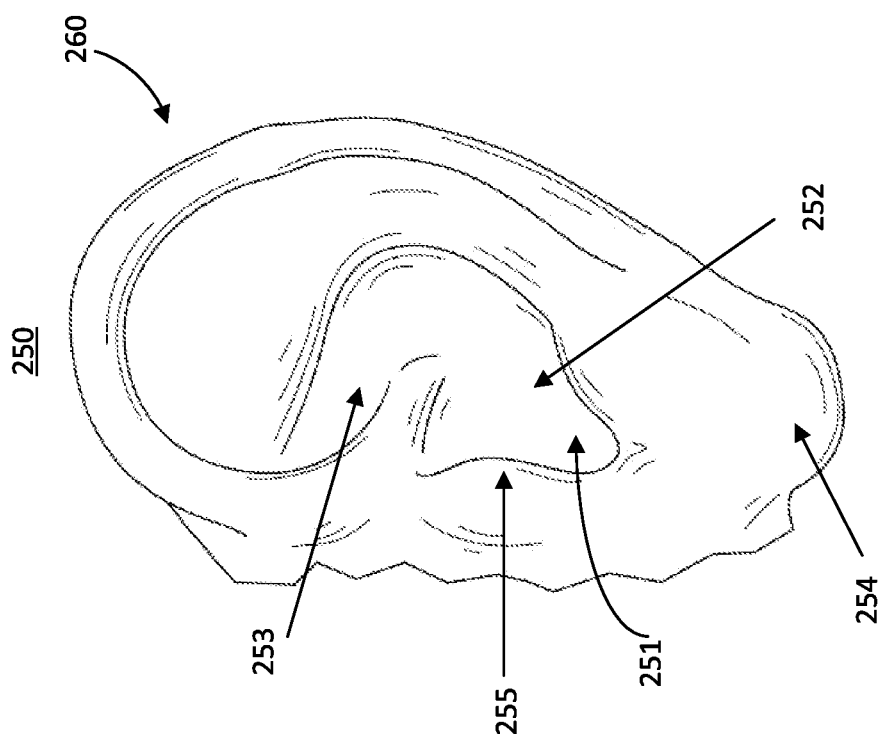
FIG. 2 includes an illustration of a masseter muscle and auricular anatomy in a human body.
Figure 2:
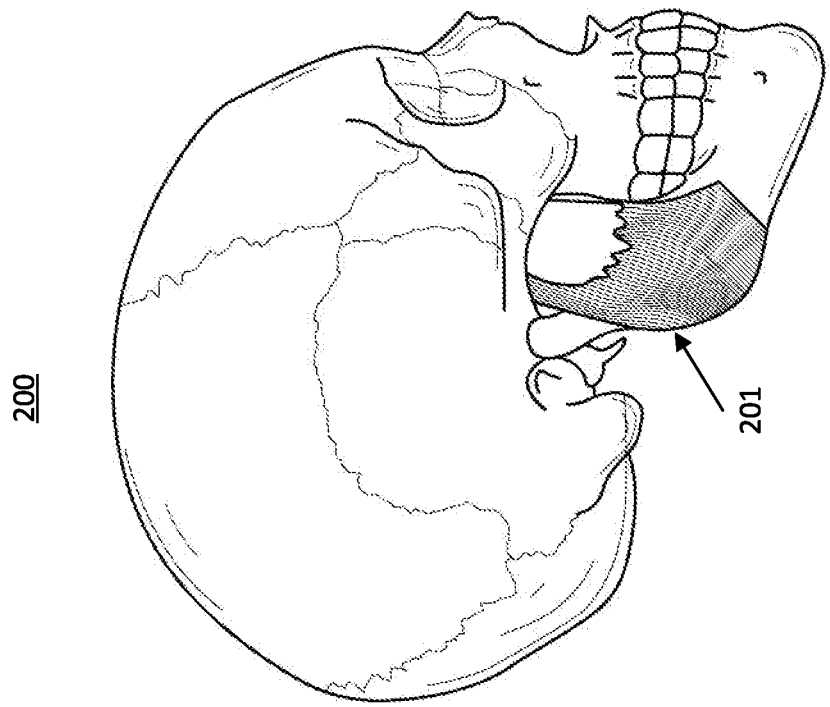

FIG. 2 includes an illustration 200 of a masseter muscle 201 in a human body. Masseter muscle contraction (or "jaw clenching", as used herein) is a voluntary action from the subject. For the purposes of this disclosure, it can be considered that the mouth of the subject is closed, with the upper and lower teeth in contact with each other, and that the subject then contracts the masseter muscles. Since the jaw of the subject is already "closed", with upper and lower teeth already in contact, there is no significant movement of the jaw per se, except for the change of shape, size and rigidity of the masseter muscle for the time of the contraction.

In specific embodiment of the invention, a muscular activity of the masseter muscle can be measured and used by a neural interface in a personal head wearable device to perform certain functions. This muscular activity can be recorded using an EMG system as explained before in this disclosure. In specific embodiments of the invention, at least one of the electrodes, such as electrodes 102 and 103, can be placed in or near the ears of the subject, hence in the vicinity of the area where the targeted electrical signal originates from, which can maximize the strength of the signal, as signal strength can decrease with the distance from the signal source).

FIG. 2 also includes an illustration of the auricular anatomy 250 in a human body. In order to measure the bioelectric signal, the electrodes can be placed in contact with the subject's skin at any location within or near the ear. For example in the ear canal 251, inferior concha 252, superior concha 253, ear lobe 254, tragus 255, etc., or around the ear 260. The electrodes can be on the surface of a wearable device, such as an earbud, so that the electrodes are in contact with the skin when the subject wears the device.

With reference back to FIG. 1, the system 100 can include a processing block such as processing block 104. The processing block can have access to a memory 105 which can be internal or external to the processing block 104. The memory can store instructions for execution by the processing unit, for example instructions to execute method steps such as steps 152 of analyzing the signal and step 153 of generating an interface signal, as will be described in more detail in this disclosure. The processing block can include any kind of processing unit such as a microcontroller, microprocessor, ASIC, FPGA, etc. The processing block can be implemented as a CPU, GPU, TPU, FPU, etc. and using any memory components, such as Flash, RAM, SRAM, ROM, etc. The processing block can be implemented by one or multiple processors operating in parallel.

The electrodes can be connected to other hardware units not represented in the figures, such as a hardware analog front end (AFE), using wires or any type of electrical connecting system. The AFE can be embedded within the device where the electrodes are operating, or external to the device (e.g. external electrical board). The AFE can contain an Analog Differential Amplifier, analog filters, analog amplifiers to add gain to the system and/or other hardware modules for further processing the signal measured by the electrodes. In cases where there are only one measurement electrode and one reference electrode, the entry of the AFE is the differential signal between the measurement electrode and the reference electrode. In cases where there are more than one measurement electrode, the AFE can have several "channels", each channel consisting in the differential signal between one measurement electrode and the reference electrode.

Besides the aforementioned "measurement" and "reference" electrodes, the system can include additional electrodes. For example, the system can include a "Bias" or "Driven Right Leg" electrode, used to cancel the common mode measured across the different channels. The system can also include a "Ground" electrode, used to establish a common ground between the electronics and the body of the subject.

The system can include an Analog-to-Digital Converter (ADC). The AFE can amplify the electrical signal recorded for each channel in order to maximize the range of the voltage of the electrical signal, for example under the constraint of the maximal voltage allowed at the input of the ADC. For instance, if the ADC allows input signals between 0V and 2V and the signal recorded at the entry of the AFE lies between −0.1 mV and 0.1 mV, the ideal AFE would apply a gain of 10 000 and an addition of a 1V DC component.

The ADC can perform a discretization of the signal, at a given sampling frequency. For instance, with a sampling frequency of 250 Hz, a discrete value of the signal is measured every 4 ms. The ADC can also perform a digitalization of the signal, according to the resolution of the ADC. For instance, if the ADC has an input range of 2V and a resolution of 10 bits, every voltage measurement can be rounded at the closest multiple of 1.953 mV ($2V/2^{10}=1.953$ mV).

The discretized and digitized signal can then be transmitted to the processing block of the system, such as processing block 104 of FIG. 1. The processing block can perform certain operations, such as signal processing operations, prediction operations, data transfer operations, etc., as will be described in more detail in this disclosure. The processing block can perform the certain operations described herein, for example by executing instructions stored in memory.

The processing block can perform signal processing operations that include, for example, filtering (highpass, lowpass, bandpass, notch or any of their combinations), slicing, padding, cleaning of artefacts using advanced techniques (e.g., ICA, Riemannian Geometry), channels recombination, channels re-referencing, etc.

The processing block can perform prediction operations that include, for example, classification label, for example to identify certain muscle contractions, identify outlier signals, etc. It can be based on either rule-based models or pre-trained supervised machine learning models (such as Neural Network, Support Vectors Classifier, Logistic Regression, Decision Trees, any Ensemble Methods or Linear Classifiers, etc.), clustering based on unsupervised methods (such as mixture models, k-means and variants, etc.), regression (such as linear regressions, Bayesian models, etc.), reinforcement learning (such as Q-learning, Monte-Carlo methods), etc.

The processing block can also perform data transfer operations that include, for example, transfer of recorded data and/or the output of any of signal processing and/or prediction to an electronic device. The electronic device can be a personal user device, such as personal user device 120 in FIG. 1, for example a smartphone or a personal computer. The electronic device can also be a distant server with which the system communicates to perform certain operations, for example further processing. The system can communicate with the electronic devices either wirelessly, for example via Bluetooth, WiFi, etc., or via a wired connection. Additional processing and display can then be performed on the electronic devices associated with the system.

In specific embodiments of the invention, the system is configured to analyze the bioelectric signal measured by the electrodes, as indicated in step 152. The bioelectric signal can be analyzed in order to recognize a gesture signal in the bioelectric signal. The gesture signal can be a signal representative of a gesture performed by the wearer as comprised in the bioelectric signal measured by the electrodes. The gesture signal can be a signal associated to gestures involving the masseter muscle contraction, such as gestures involving the jaw clenching described above.

In specific embodiments of the invention, specific gesture signals for specific gestures can be recognized by the system from the bioelectric signal measured by the electrodes. One gesture can be a "double jaw clenching", where the subject clenches the jaw twice. There can be a delay between each clenching, which can be a predetermined delay or a delay subject to a threshold. For example, the delay can be set to be less than 1 s, and could be refined if needed, for example to 0.8 s. Another gesture can be a "triple jaw clenching", where the subject clenches the jaw three times. There can be delay between each clenching, which can be a predetermined delay or a delay subject to a threshold. For example, the delay can be set to be less than 1 s, and could be refined if needed, for example to 0.8 s. Another gesture can be a "long jaw clenching", where the subject clenches her jaw and keeps her masseter muscles contracted for a period of time, which can be a predetermined period of time, for example at least 1 s. Therefore, in specific embodiments of the invention, the gesture signal to be recognized in the bioelectric signal can be one of a double jaw clenching signal, a triple jaw clenching signal, and a long jaw clenching signal.

The reason for choosing the above-mentioned gestures instead or a "single jaw clenching" for instance, where the subject clenches the jaw once, is that those gestures can produce a gesture signal with characteristics that are more easily discernible from common gestures performed by a subject (e.g., chewing, swallowing, talking, etc.)

In specific embodiments of the invention, the system is configured to generate an interface signal upon recognizing the gesture signal in the bioelectric signal, as indicated in step 153 of flowchart 150. The interface signal can alternatively or in combination be a feedback signal to notify the user that the gesture was recognized, a control signal for the wearable device or an associated device, or a training signal used to train a gesture recognition model for the gesture recognition system.

The interface signal can be a feedback signal for the user that the gesture signal was recognized. The feedback can be in the form an auditory, visual or haptic feedback, such as a beep or hearable message, a message on a display, a vibration, etc. The user interface output can be located on the personal head wearable device itself. For example, the user interface output can be the speaker 106 of device 100. Alternatively or in combination, the user interface output can be a vibrator or display on the wearable device. Alternatively or in combination, the user interface output can be located on a device operating in conjunction with the personal head wearable device, such as personal user device 120. For example, the interface signal can be a representation of the gesture signal displayed on a display 128 or auditory message via speaker 126.

The interface signal can not only be an explicit feedback that the gesture has been recognized but also a control signal for the system and/or other devices associated with the system. For example, the control signal can be used to perform certain actions or trigger certain events for devices associated with the system depending on the gesture performed by the user as recognized from the gesture signal. In this way, the interface signal can be used to control a play/pause function, a start/end call function, and the like. As a result, a system in accordance with specific embodiments of the invention can be used to control devices, including hands-free control.

Electronic devices, such as personal user device 120 of FIG. 1, can then be controlled by performing gestures and recognizing the gesture signals in the bioelectric signal. Several control functions can be performed by using the system described herein, such as play/pause music, for example using True Wireless earphones, open/close push-to-talk communication on a walkie talkie, grasp an object using VR Headset, trigger noise cancellation on sleep buds, trigger ASSR test on hearing aids, among others.

The gesture signal in the bioelectric signal can be recognized using a stored signature model for the gesture signal. In specific embodiments of the invention, the stored signature model can be a default signature model associated with the gesture. The default signature model can be configured based on distinctive bioelectric signal patterns, in the time domain and/or in the frequency domain, that are characteristic with the gesture. Advantageously, the default signature model is based on bioelectric signal patterns similar from person to person. The default signature model can be pre-stored within the system or in an external device, such as a server, that processes data for the system. The default signature model can be a neural network that has been trained with data from multiple gesture signals so that a gesture performed by the user can be predicted. The default signature model can be a classifier with stored signatures for gesture signals embedded for example as weights of a neural network or variables in a function.

The default signature module can be calibrated for example via a training process, an adaptive learning process, domain shifting, or other parametric or non-parametric methods. During the training process, a user can interact with the system and provide data so that the system can "learn" from the specific user and refine the default model accordingly. In this way, the default signature model can be adjusted to the individual users as the users can update their stored signature model, as will be described in more detail below.

In specific embodiments of the invention, the system is configured to generate a prompt to perform a gesture associated with the gesture signal and update the stored signature model using the gesture signal to generate a revised stored signature model. A revised stored signature model is a stored signature model that has been calibrated with data from a training process performed by the user.

The training process can be performed the first time that the system is used so that the system can "learn" the gestures properly, for example when a wearable device is used for the first time. The training process can be performed additional times if a user desires to adjust the model (for example if the user realizes that performing the gesture in a certain way is not triggering the desired outcome). In this way, the system can be calibrated to improve the performance of gesture detection algorithms and improve the user experience when performing the gestures.

A training module can provide the user with a procedure to learn to perform clear muscular jaw movements for the purpose of activating the neural interface. The training module can be configured so that the user is prompted to perform a particular jaw gesture. The user can try to perform the jaw gesture, and a feedback signal can be generated when the particular jaw gesture is detected by the neural interface. The feedback signal can be for example, displayed on a graphical user interface displaying a measured signal, played back as an auditory feedback signal (e.g., a beep played by speakers on the wearable device) and/or provided in the form of a haptic signal (e.g., earbud vibrating). The user can therefore refine the jaw gesture to improve the performance of the gesture recognition system.

Figure 3:
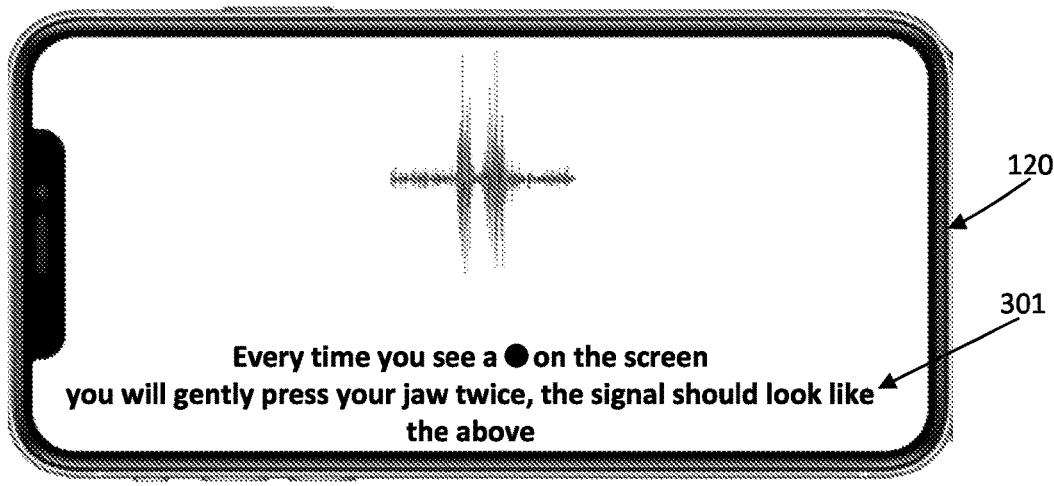
FIG. 3 includes examples of screens provided on a display during a training process of the system, in accordance with specific embodiments of the invention disclosed herein.
Figure 3:
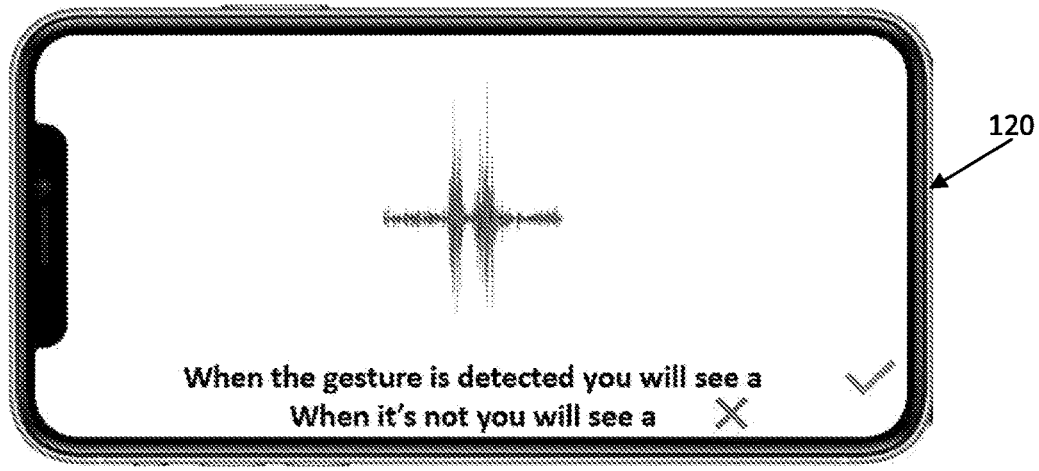
Figure 3:
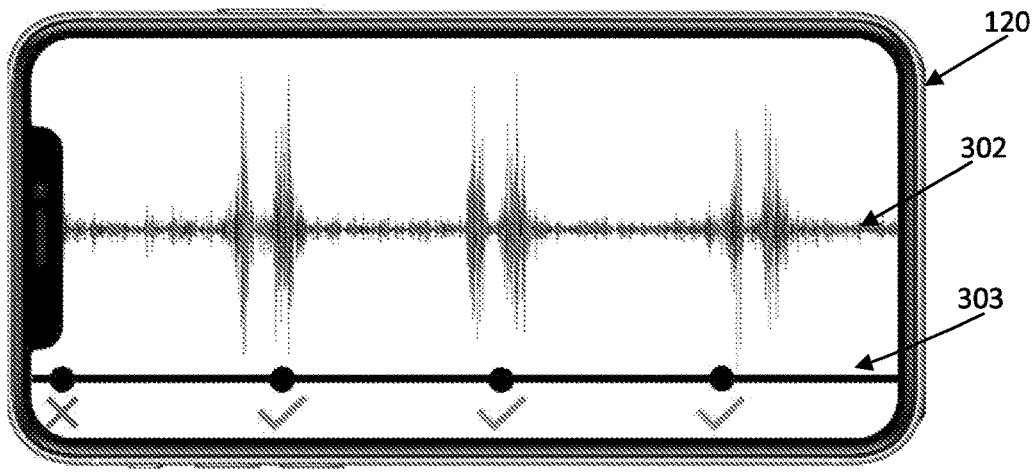

The training process can be aided by a companion application running on a personal user device such as personal user device 120. The application can be associated with the system so that the system can output and input data via the application even when the application is running on a device that is not part of the system. In this way, the user may be wearing the head wearable device for signal recognition and looking at the process on an external device. FIG. 3 include examples of screens provided, for example, by the companion application running on the personal user device 120. The user could install and open the companion application in the personal user device. The personal user device could provide a notification to open the application when a connection with the wearable device is detected. As a first step in the training process, the system, for example via the application, could provide information as to how the technology behind the system works. This step could include video and animations showing the masseter muscles contraction, pictures and messages explaining that electrodes are used to record facial activity, and that technology such as Artificial Intelligence transforms the signals into actions by the system. In a subsequent step, the system can check if the wearable device is properly connected to the skin of the user and if the SNR is good enough. The system could, for example via the application, provide notifications as to the correct placement of the electrodes, and ask the user to move or clean the device if it doesn't work.

The application could also provide an explanation about the gesture to be performed. Screen 300 includes an example of a screen in a personal user device 120 with an explanation of the process that the user may follow. A message, such as message 301, can be displayed on a screen of the personal user device or be an audible message provided via a speaker of the personal user device or the wearable device itself. The application can also provide an explanation about the feedback to be given to help a user understand what the right gesture is. Screen 310 includes an example of a screen in a personal user device 120 with an explanation of the feedback that the user may receive.

Two options can be done independently or sequentially and repeated as many times as the user wants. First, the user starts the test and can be asked to perform a gesture for example for 1-2 minutes every 3-10 seconds and receive feedback appropriately. Second, the user can be asked to perform the gesture whenever he/she wants over the course of a period of time, for example a 1-2 minutes trial and receive feedback appropriately. Screen 320 includes an example of a screen in a personal user device 120 with a plot of the signal 302 as it is being measured by the electrodes, and feedback signal 303 provided by the system as the gesture is detected.

After the system has been trained, the model has been otherwise updated and/or the signature associated with the gesture signal is properly stored, this stored signature model can be used by the system to find the gesture signal in the bioelectrical signal measured by the electrodes, by using the stored signature model. The system can include specific hardware modules or software routines to perform such recognition. The use of the signal processing modules described above allows the system to process the data from the signal measured by the electrodes and provide predictions based on such data, as will be explained below in more detail. The recognition can be aided by artificial intelligence.

The system can include various means to provide feedback to the user. For example, the system can include one or more speakers. If the system is embedded in an earbud, the speaker can be a speaker of the earbud, such as speaker 106. If the system is associated with another device, for example a personal user device connected to such earbud, such as device 120, the speaker can be a speaker 126 of the mobile device. The system can include a display, for example a display 128 of the personal user device, that can also be used to provide feedback to the user and to receive data from the user. In embodiments in which the wearable device has its own display (e.g., a smartwatch) the feedback could be provided on that display. The system can include other hardware modules capable of providing feedback, for example lights, vibration hardware, etc.

During the training process, different types of feedback can be provided to help the user throughout the process. As an example, a visual feedback can be provided. The visual feedback can be provided by using the display of the personal user device or other kind of visual indications, such as lights. For example, a color code can be used to indicate the state of the process. In a specific example, grey color can be used by default and turn into green when a gesture is detected. In this way, the user has a clear indication that the system is recognizing the gesture. As another example of a visual feedback, the system can be configured to display, for example on a display of the personal user device, a plot of the bioelectric signal as measured by the electrodes. An example was illustrated in screen 320 of FIG. 3, where the plot of the signal 302 is displayed while the user performs the gestures. The apparition of the bioelectric signal, as measured by the electrodes, on a screen can help the user detect what happens when the gesture is performed in different ways, for example with more or less strength. As another example of a visual feedback, the system can display an indication mimicking the strength of the bioelectric signal measured, such as a gauge for this purpose. An example of a gauge for feedback signal 303 is also illustrated in screen 320 of FIG. 3.

Another kind of feedback that can be provided by the system can be an audio feedback. An example of an audio feedback can be a chime, a ping, or any kind of sound that is performed when the gesture is detected by the system. In specific embodiments, the sound can be weak or strong depending on the strength the gesture is performed at, similarly to a sonar.

Another kind of feedback that can be provided by the system can be a haptic feedback. An example of haptic feedback can be a simple vibration when the gesture is detected by the system. In specific embodiments, the vibration can be a weaker or stronger vibration depending on the strength the gesture is performed at.

As mentioned before, the electrodes can be on an exterior surface of a wearable device. The wearable device can be an earbud. The system can include additional wearable devices, such as wearable device 110 in FIG. 1, which can be for example a second earbud. The second earbud can also be provided with electrodes, such as electrodes 112 and 113, that measure the bioelectric signal, in the manner described above with regard to the first earbud. The electrodes of the second earbud can also be on an exterior surface of the second earbud in the manner described herein for the first earbud. In those cases, the recognizing of the gesture signal in the bioelectric signal can use a combination of data measured by electrodes of the first earbud and data measured by electrodes of the second earbud. The second earbud 110 can include the same or similar components as described with reference to the first earbud of the system 100. For example, the second earbud can include a processing block 114, memory 115, and speaker 116, among other components.

In specific embodiments of the invention, one or more electrodes can measure the bioelectric signal independently. The measurements can be conducted relative to a reference electrode. In specific embodiments, the multiple measurements can be analyzed to determine a common mode signal for the system (e.g., the multiple measurements can be summed and averaged). The multiple measurements can be conducted relative to a single reference electrode or more than one reference electrode. In specific embodiments, the system can be designed to generate an opposite of the common mode signal and feedback the signal into the body of the wearer to counteract the common mode signal. The measurement and generation of the common mode and opposite signals can be conducted continuously to improve the performance of the system. The signal used to cancel out the common mode signal could be fed back using an electrode which can be referred to as a driven-right-leg electrode.

In specific embodiments, one or more distinct elements of the gesture recognition system (e.g., two separate earbuds or earpieces) can include different numbers and configurations of electrodes. In embodiments in which the electrodes number two, one electrode could be the reference electrode and one electrode could be the measurement electrode. In embodiments in which there were more than two electrodes the third could be another measurement electrode, a driven-right-leg electrode, or a ground electrode. In a specific embodiment of the invention, a system could include two elements which each include three electrodes for a total of six. In these embodiments, one of the electrodes on each of the two elements could be a reference electrode for the other electrodes on that element. In specific embodiments of the invention, the two distinct elements can be wired together or be connected via a wireless communication link. For example, two ear buds could each include two electrodes and the two ear buds could be wired together. In this embodiment, the wire could be used to allow the two devices to act as a single measurement system with the measurements by each device being performed jointly to produce a more accurate reading. In a system comprising two earpieces wired together and at least three electrodes, multiple alternative configurations are possible including: 2 measurement electrodes in the first ear, 1 reference electrode in the second ear; 1 measurement electrode and 1 reference electrode in the first ear, 1 measurement electrode in the second ear; 1 measurement electrode and 1 driven-right-leg electrode in the first ear, 1 reference electrode in the second ear; 1 measurement electrode and 1 reference electrode in the first ear, 1 driven-right-leg electrode in the second ear; 1 reference electrode and 1 driven-right-leg electrode in the first ear, 1 measurement electrode in the second ear; 1 measurement electrode and 1 ground electrode in the first ear, 1 reference electrode in the second ear; 1 measurement electrode and 1 reference electrode in the first ear, 1 ground electrode in the second ear; and 1 reference electrode and 1 ground electrode in the first ear, 1 measurement electrode in the second ear.

Figure 4:
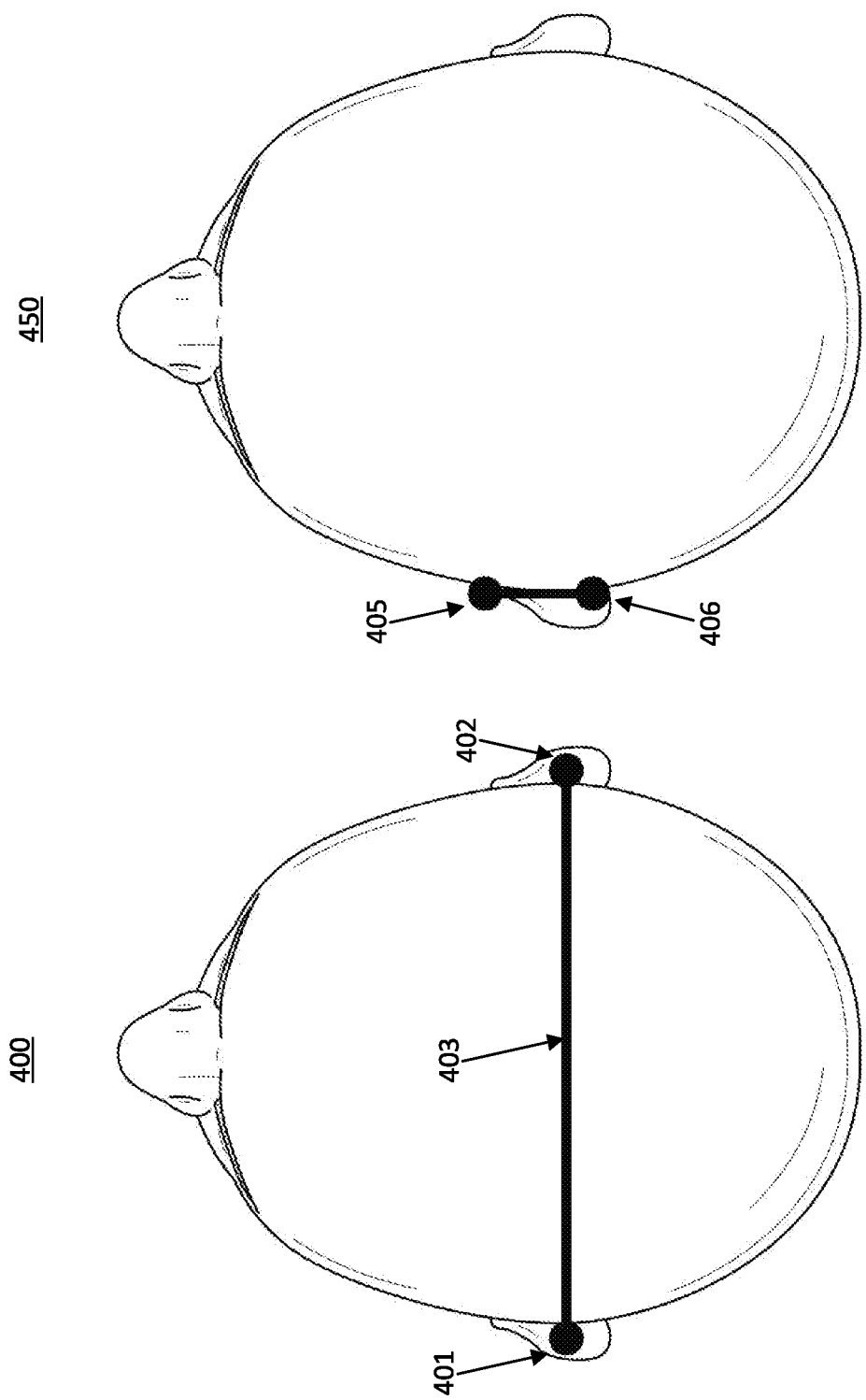
FIG. 4 includes an example of a cross-ear configuration and a single-ear configuration, in accordance with specific embodiments of the invention disclosed herein.

FIG. 4 includes an example of an embodiment 400 including two earbuds, 401 and 402, connected by a wire 403. In embodiments where the two earbuds are connected using a wire, the system comprising the two earbuds and all the electrodes they contain can be considered as a single electrical system, and only one reference electrode can be used for the whole system. Each channel can receive the differential signal between one measurement electrode and the reference electrode as explained before. All channels can be processed simultaneously in a synchronized way by the same ADC, and the signal processing and prediction steps can take signals from all channels as an input. By taking into account all channels together, the quality of signal processing (e.g., noise removal) and the prediction can be improved.

From a general perspective, the more the measurement electrode and the reference electrode are distant from each other, the better the signal. Hence, this setup allows for reference electrode in one ear, and one or several measurement electrodes in the opposite ear, which can lead to a better signal quality compared to having measurement electrodes and the reference electrode in the same ear. However, when the electrodes are mounted on True Wireless Earphones (TWS) for instance, there can be no wired connection between the two earbuds. In those embodiments, each earbud can be considered as an independent electrical system. As such, in specific embodiments, a measurement electrode or electrodes and their reference electrode are on the same ear, which can lead to decrease in signal quality. FIG. 4 also illustrates an example of an embodiment 450 including a single earbud as an independent system, with the electrodes 405 and 406 located on the same ear. When a second earbud is also used in this configuration, the electrodes of each earbud will provide individual measurements of the bioelectric signal.

In embodiments in which multiple earbuds provide independent measurements, various recombination solutions can be implemented for combining the data from the different earbuds. In specific embodiments of the invention, recombination of predictions can be used. With this solution, the signal processing and prediction steps described above can be run independently on each earbud, and predictions from both earbuds can be combined in various ways. For instance, if one earbud predicts a jaw clenching detection with a probability of 0.60 and the other earbud predicts a jaw clenching detection with a probability of 0.80 those probabilities can be averaged and it can be assumed that a jaw clenching has been detected with a probability of 0.70. This solution could be advantageous in that since each earbud remains an independent system, the subject can enjoy the system functionalities when wearing only one earbud.

In specific embodiments of the invention, recombination of features can be used. This solution consists in, when a Machine Learning model based on pre-computed features is used (e.g., Support Vector Classifier, Logistic Regression, etc.), computing those features independently on each earbud and then combining them. The features can be combined by averaging the value of a given feature between both earbuds. For example, feature A has value 3.0 for one earbud and 5.0 for the other earbud, then a feature A of 4.0 can be passed to the model for prediction. As an alternative, the features can be combined by having a duplicate feature passed to the model. For example, feature A1 and feature A2, as obtained from separate earbuds, can be passed to the model, and the model can be trained to handle twice as many features in that case.

In specific embodiments of the invention, recombination of signals can be used. This solution consists in recombining signals from both earbuds before the signal processing step, or after the signal processing step and before the prediction step. In specific embodiments of the invention, the ADCs of both earbuds may not be synchronized (i.e., the discretized values measured by each ADC may not be recorded at the exact same instants, and this delay can vary across the different usages of the device). In that case, some preprocessing steps may be performed, such as shifting and resampling of the signal to maximize the correlation between signal windows observed from each earbud.

The recombination steps described above can be performed either by the embedded software of either earbud, or by an external electronic device (e.g., personal user device such as smartphone, laptop). In case the recombination is done on the earbuds, and both earbuds are worn together, one earbud can act as the "master" and collect the predictions/features/signals from the other earbud to perform the recombination. Whether the recombination is performed on the earbuds or on an external device, the system can be able to determine whether both earbuds are being used or not and adapt accordingly.

In specific embodiments of the invention, the system is configured to determine if the bioelectric signal is present in the data from a first set of electrodes, for example from a first earbud and in the data from a second set of electrodes, for example from a second earbud. The recognizing of the gesture signal in the bioelectric signal can use the combination with the stored signature model if the bioelectric signal is present in both the first data and the second data and can use only one of the first and second data with the stored signature model if the bioelectric signal is present in only one of the first data and the second data. In this way, if one of the earbuds is not being used, or if contact with some electrodes is lost, the system can still perform the intended functions with the data that is left.

In specific embodiments of the invention in which multiple sample signals are collected on either side of a wireless link (e.g., two wireless earbuds connected by a Bluetooth connection) it can be beneficial to avoid sending raw data from one ear to the other through a communication connection. Rather than sending raw data, in specific embodiments of the invention local processing can be performed on each side and combined to make a better signal detection prediction. Predictions from "processed signals" can be combined, for example via voting systems or averages. Data from two sides can be combined to make a single prediction by providing, by each side, a probability (not a 0 or 1). The probabilities can be added together and then a threshold can be applied. Combining preprocessed signals (i.e., raw data) can also be performed by determining an average of signals or training a model to make predictions with 2 electrodes (or more) as input.

In specific embodiments of the invention, the system can be configured to sample the bioelectric signal using a sliding window. The system can perform the recognition of the gesture signal in the bioelectric signal using data from the sliding window. The sliding window can have a predefined period, for example a period of one to three seconds. The sliding window can have a predefined sample interval, for example from 0.1 to 0.5 seconds.

The electrode signal can be sampled at different times. A sampler can be applied to a series of samples. The sampler can be applied in a temporal domain (a convolution) or in the frequency domain (a fast Fourier transform, multiplication by coefficients, and reverse fast Fourier transform). The series of samples can span a period of time ranging from 1 to 3 seconds (e.g., a 2 second window of time). The 1 to 3 seconds window range is a tradeoff between computation resource, accuracy, and response time. Indeed, a longer observation window (e.g., 20 seconds) would provide a clear jaw clenching signal, but too slow (latency) and computationally heavy. Yet, a 2 second window of time is a long response time (latency), not acceptable in most situations. In order to reduce the latency of the detection, the window of samples can be "sliding" by small increments, such as 0.2 second. In other words, every 0.2 second, the older 0.2 seconds samples are deleted, the samples are shifted by 0.2 seconds and the next 0.2 seconds of samples are added. The sampling can be performed with a trained artificial intelligence (AI) model.

Figure 5:
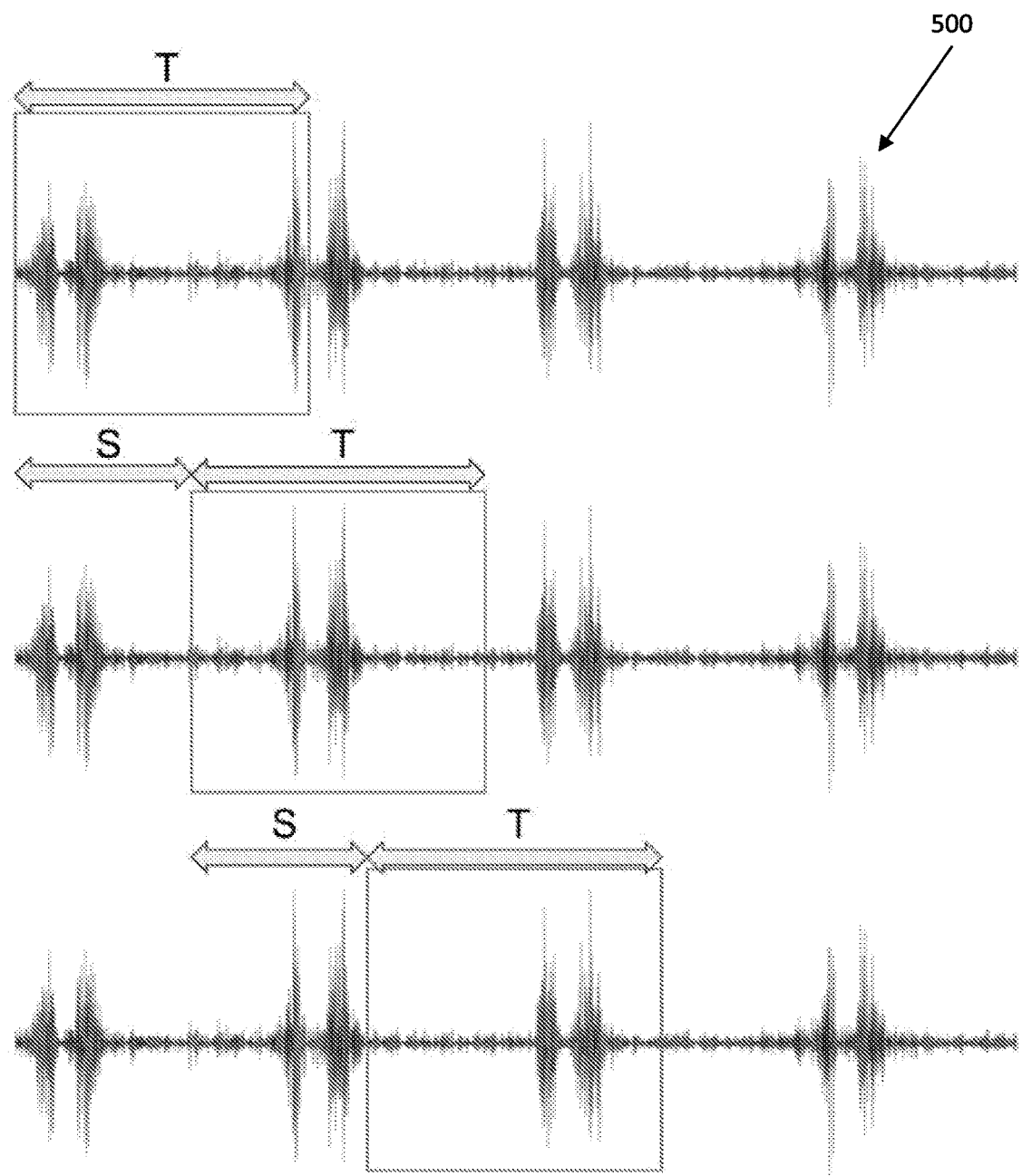
FIG. 5 includes an example of a double jaw clenching signal as measured by the electrodes and a sliding window, in accordance with specific embodiments of the invention disclosed herein.

In specific embodiments of the invention, the system can record EMG data continuously, for example measuring one new bioelectric signal value for each channel every $1/F_s$ seconds (Fs being the sampling frequency). For instance, for Fs=250 Hz, one value is measured every 4 ms. To perform signal processing and prediction operations, the system may require a window of fixed length in input. For instance, with Fs=250 Hz, the system could take as an input a window of fixed size N=500 data points for each channel, which corresponds to T=500/250=2 s of signal. Since the system is recording EMG data of the subject continuously, it makes sense to update the time window so that it includes the latest data recorded by the system, but still contains N data points. A solution for that purpose is to use a sliding window. FIG. 5 includes an example of a double jaw clenching signal 500 as measured by the electrodes. FIG. 5 includes an example of a sliding window of length T, that can be updated at a regular time interval of S, as applied to the signal 500.

A long window size (T large) can allow observation of a phenomenon (e.g., the double jaw clenching as shown in the figures), as well as what happened before and after over a longer period of time. This is likely to improve the accuracy of a system that aims at detecting such phenomenon, because this can help to avoid confusion with other phenomena that could have a very similar footprint on a shorter time window. On the other hand, a long window size could imply that the signal processing and prediction operations require more processing time and/or power, since the number of operations performed by the processing unit can be higher.

If there is a limit of computing power imposed by the hardware (e.g., embedded system that has limited computing power and memory), then the processing time can be increased, and so can the delay before the system can return a prediction. This can be an issue if the system needs to respond as fast as possible (e.g., if the system is used to play/pause music, it is not desirable to wait too long between the moment that the jaw clenching gesture is performed and the moment the music plays/pauses). Choosing hardware that is able to allocate significant computing power to keep processing time in a decent range with large windows can be challenging, especially when there are constraints of size and battery consumption.

In the specific embodiments described with reference to FIG. 5, the system can compute a new signal processing and prediction operation every S seconds. If S is large, there can be some additional delay before the system detects the phenomenon. For instance, if S=3 s, the phenomenon may be detected up to 3 s after the gesture was actually performed. Hence having a short time interval S can allow to decrease the response time of the system. On the other hand, a short time interval S also means that the system may have to compute signal processing and prediction operations more often, which can be subject to the potential computing power and battery consumption constraints already expressed. For the purposes of this disclosure, it is estimated that using a window of T between 1 and 3 seconds, and a time interval of S between 0.1 and 0.5 seconds can be a good range. This is not a limitation of the present invention as other ranges can be used depending on the specific capabilities, desired outcome, and constraints of the specific system.

In specific embodiments of the invention, the system can be configured to operate in specific modes. For example, the system can be configured to operate in a low-power high sensitivity mode and/or a higher-power high accuracy mode. The system can be configured to switch between the modes depending on specific factors such as events or the status of the system. For example, the system can be configured to detect a potential gesture signal in the low power high sensitivity mode and trigger a higher-power high accuracy mode upon detecting the potential gesture signal.

A prediction model that has very good performances (in terms of precision and recall) is likely to be quite sophisticated, and hence to consume more processing power compared to a very basic prediction model (like comparing signal amplitude to a predefined threshold for instance). Running such a sophisticated model constantly (for every input time window) can harm battery life and is often not useful as the user may not perform the gesture of interest for long periods of time. To mitigate that issue, specific embodiments of the invention refer to a system that can constantly run a much simpler model (in a low-power high sensitivity mode) that can have poorer precision but good recall (i.e., this model can predict a lot of false positives, but verify few false negatives). Then, when this simpler model predicts a positive, the more sophisticated model can be run (in a higher-power high accuracy mode) to refine the prediction. By doing so, the impact on battery life can be limited significantly.

The simpler model (low-power high sensitivity mode) can be implemented in various ways. The model can consist in very simple operations like thresholding. For example, if the maximal voltage amplitude observed in the signal window is above T, then the more sophisticated prediction model (higher-power high accuracy mode) can be triggered. The model can take as an input windows that are much shorter, and hence the number of computing operations can be drastically diminished.

Regarding the more sophisticated model (higher-power high accuracy mode), it can be trained offline, for example on signal windows such as the sliding windows of FIG. 5. This model can be intended to be high precision and high recall, to give the best prediction possible. To maximize the performances of such model, signals from both ears can be combined as described before in this disclosure. Additionally, the model can be run on successive sliding windows, and average prediction probabilities. If all the time windows contain the phenomenon, averaging prediction probabilities can reduce variance on the prediction, which is likely to improve the result. A potential downside of this solution is that it can increase the response time between the moment when the gesture is performed and the moment when the positive prediction is triggered. For instance, if the predictions for 3 successive 2 s-windows taken every 0.2 s are considered, averaging those 3 predictions will most likely increase confidence in the overall prediction, but the wait would be of 2×0.2 s=0.4 s before the control is triggered.

The more sophisticated model can be trained to detect a phenomenon in a given time window. In this way, if the same phenomenon is present in successive windows, nothing will prevent the system from triggering a positive prediction for all those windows. There are several ways to mitigate that issue. For example, if the algorithm used provides a way to locate key descriptive features (e.g., peak detection), then it can be detected whether the phenomena detected in successive windows correspond to the same realization. As another example, a buffer period can be defined, for which no positive prediction is triggered after a phenomenon has been positively detected.

In specific embodiments of the invention, the system can further include a filter for filtering the bioelectric signal as measured by the electrodes, such as filters 109 and 119. The filter can include at least a high pass filter response. In specific embodiments of the invention, the high pass filter response can have a cutoff frequency below 90 hertz. In specific embodiments of the invention, the high pass filter response can have a cutoff frequency between 50 hertz and 90 hertz. The cutoff frequency can delineate a pass band of the high pass filter (above the cutoff frequency) from a stop band of the high pass filter (below the cutoff frequency). In specific embodiments, the cutoff frequency can be the −3 dB frequency of the filter response meaning that at the cutoff frequency the filter has already attenuated the signal to −3 dB relative to the filter response in the pass band. The filter can alternatively or in combination further include at least one notch filter response to attenuate signals. The attenuation can be within the pass band of the high pass filter response. For example, the filter can include notch filters which attenuate signals with frequencies of 100 hertz and/or 120 hertz. In specific embodiments of the invention, the at least one notch filter response can have a notch that includes at least one of 100 hertz and 120 hertz. The filter can be an analog, digital or mixed signal filter.

EMG signals mostly carry frequencies in the range of 50-500 Hz, with higher concentration in 50-150 Hz. To be able to observe those phenomena, an appropriate sampling frequency can be selected for the ADC. As per the Nyquist-Shannon theorem, a sampling frequency Fs allows to observe phenomena in the range 0 Hz to Fs/2 Hz without aliasing. Hence a sampling frequency as high as possible can be selected. On the other hand, a high sampling frequency can imply high memory and computation time needed to process a window of signal. A good tradeoff can be to pick a sampling frequency not below 125 Hz (otherwise it can be very difficult to observe proper EMG signal) and not above 300 Hz (as most of the signal of interest is likely to lie below 150 Hz). In specific embodiments of the invention, electrode signals can be sampled around 250 Hz, at least 125 Hz, and below 500 Hz. This is a tradeoff between not too high to limit the data set (below 500 Hz), and not too low to detect EMG signal based on Nyquist (at least 125 Hz).

EMG systems can be affected by surrounding electromagnetic perturbations. The most common can be caused by the domestic electrical network, which generates a perturbation at 50 Hz and its harmonics in Europe, and 60 Hz and its harmonics in the US for instance. This noise can overlap with the EMG frequency range. Specific embodiments of the invention use a filter to remove this noise so as not to pollute the EMG signal.

The filters can be implemented in various ways. For example, the filters can be implemented using analog components (R, L, C components, with or without operational amplifiers for active gain) that perform filtering on analog signals. As another example, the filters can be implemented using numerical functions that take as an input the discretized and digitized signals that come out of the ADC. There are many libraries implementing such filters, with the two great families being FIR (finite impulse response) and IIR (infinite impulse response) filters, and with all sorts of strategies to perform prerequisite operations on signal windows (e.g., padding, FFT, etc.).

Specific embodiments of the invention consider frequencies above 60 Hz only, using for instance a high pass filter with a cutoff frequency between 65 Hz and 80 Hz, depending on how good the attenuation of the filter is around the cut-off frequency. This can allow removal of the perturbations induced by either 50 Hz or 60 Hz noise. To mitigate the impact of the harmonics (e.g., 100 Hz, 120 Hz), specific embodiments of the invention use notch filters, that are basically band-stop filters with a very narrow rejection band centered around a given frequency. This can leave most of the signal at other frequencies unaffected.

The filters utilized herein can be numerical filters having various forms. For example, a window of coefficients that can be applied using convolution with the signal in the time domain, or a window of coefficients that can be applied using pointwise multiplication with the signal in the frequency domain. In any case, the more accurate the filtering desired, the longer the window of coefficients can be. For example, if a notch filter at 100 Hz is applied, using a convolution in the time domain, with a 20 dB rejection band of 1 Hz (i.e., the signal is attenuated by 20 dB or more between 99.5 Hz and 100.5 Hz), the window can be significantly longer than if the same filter but with a rejection band of 3 Hz is applied. These considerations can have implications. For example, if the coefficients window of the filter is significantly longer than the length of the signal windows analyzed, the result of the filtering operation may be suboptimal. Additionally, long filter coefficients window can imply a high computation load, which can present issues with highly constrained embedded systems.

In specific embodiments of the invention, instead or in conjunction with a notch filter, it is possible to apply a high pass filter between 60 Hz and 80 Hz. For example, a high pass filter at 60 Hz (to remove the 50 Hz), or a high pass filter at 65 Hz (to remove both the 50 Hz and the 60 Hz), or a high pass filter at 80 Hz (to avoid any leak if the filter is with a low temporal window, low computation power). It can be also possible to combine a high pass filter (60 Hz-80 Hz) and one or more notch filters for the harmonics (100 Hz, 120 Hz, 150 Hz, 180 Hz, etc.).

In specific embodiments of the invention, the system can be configured to detect an event or state of the system, such as for example a connection and/or an idle state. The system can be also configured to transmit raw data of the bioelectric signal, or derivatives thereof, upon the detecting, for the purpose of uploading the raw data or derivatives thereof for training the algorithm for example. The raw data or derivatives thereof may then be processed on a server to clean the data or label it for training. The data can then be used to retrain the model and be pushed out to a network of wearable devices that utilize an older version of the model. The derivatives described herein can also be used locally to train the model on the wearable device and do not necessarily need to be transmitted remotely.

The derivatives of the raw data can include training labels that have been implicitly harvested from the raw data and the usage of the device. For example, the raw data can be used to perform automated baseline adjustment (i.e., a passive calibration of the signal based on the evolution of the normal or average activity measured). In which case the derivative would identify the data as average baseline data. As another example, data collected unrelated to specific events could be processed using unsupervised learning methods (e.g., clustering to identify potential positive and negative examples, review them manually and add them in the training set with the right label). As another example, data preceding a usage of the "pause music" or the "play music" on an accompanying interface (e.g., the touch screen of a smartphone paired with the model device) is likely to contain a false negative example (command was not triggered using the jaw clenching). The derivative of the raw data in this case could be a label marking it as a "positive" example in the training set. As another example, data preceding a usage of similar interface elements on the accompanying interface which override a recent interface signal generated by the gesture recognition system are likely to contain a false positive example. The derivative of the raw data in this case could be a label marking the associated raw data as a "negative" example in a training set. Likewise, the usage of a "back-up" input on the haptic controls of ear buds with a gesture recognition component could be used to generate a derivative of the raw data in a similar form. In still further examples, the model can identify raw data associated with inferences with a high degree of uncertainty and mark them for use as training data utilizing an active learning approach.

The raw data can be unprocessed data from the bioelectric signal as recorded by the electrodes. The raw data can be anonymized before transmission and can be sampled. The raw data can be uploaded to an external device or server for processing. In this way, an external system can improve the "generic" detection model, such as the default stored signature model, based on a lot of anonymized user data. Some active learning parameters (e.g., signals that were recorded around the detection event) can be included. Active learning parameters are for example other UI signals, such as if the user uses another interface (touchscreen or haptic) to do an action to be otherwise triggered by a gesture, such as play/pause, this could be indicative of a false detection of a jaw clenching.

The neural interface can be configured for storing raw data and derivatives directly locally in the earbud, with offline synchronization with an external device when there is bandwidth and/or connection available. The raw data recording (from time to time) for offline sharing during idle time (even if it is partial signals) can be used to train algorithms later (for millions of users).

The system can be able to collect data and share it with external electronic devices, such as for example a personal user device (e.g., smartphone, distant servers, etc.). The system contains memory components (e.g., Flash) that can be used to store raw data, collected for example at the output of the ADC. In that case, the memory component can be chosen to fit size and consumption constraints. These data can be sent to the external device during some predefined synchronization periods (e.g., when the device is plugged for charging, when memory occupied reaches a certain threshold, etc.). The synchronization can be done either in a wireless manner (e.g., Bluetooth, BLE, WiFi) or using a wired connection (e.g., USB-C, Micro USB).

In specific embodiments of the invention, the system can also stream raw data or derivatives thereof to an external electronic device continuously in a wireless manner. In that case, depending on the power consumption induced by such streaming and the consumption constraints of the device, various strategies may be applied together or separately, like for instance only stream data when battery is above a certain threshold, only stream X minutes of data every Y minutes, etc.

In specific embodiments of the invention, the system can not only collect raw data, but also potential "annotations" regarding these data. The annotations can be examples of the derivatives mentioned above. For example, the system can offer a way for the user to specify that there was false positive or false negative prediction. For example, with wireless earphones, some combination of haptic controls could be configured by the user to specify that a play or pause command on the music was wrongly activated.

In specific embodiments of the invention, raw data can be used for an online adjustment of the model for a particular user by using a passive calibration procedure. In specific embodiments of the invention, the system could be configured to determine an average power of the bioelectric signal when no gesture signal is recognized and normalize the bioelectric signal using the determined average power. For example, every X minutes the average power B of the bioelectric signal could be measured. Assuming that the model was trained with an average power level A, the power of the bioelectric signal could be multiplied by a factor A/B to normalize it in real time.

In specific embodiments of the invention, the stored signature model is a classifier. The classifier can be implemented as a hardware module, such as for example a processing block implementing a neural network. In this way, the stored signatures can be embedded in the classifier by for example being associated to the weights of the network. The classifier can be implemented in software, for example in the form of a function to be called by the processing block. In this way, the stored signatures can be embedded in the classifier by for example being associated with variables of the function.

The classifier can be a binary classifier and outcome "yes" or "no" to a query such as if an input gesture signal corresponds to the stored signature. The classifier can also outcome a probability as to whether there is a potential match between an input gesture signal and a stored signature. The classifier can also outcome a probability as to which stored signature is most likely to correspond to the input signal.

A set of false positive gesture signals can also be embedded in the classifier. The false positive gesture signal can be signals detected from gestures that are not the gestures to be captured by the system such as a chewing signal, a talking signal, a swallowing signal, a lateral head movement signal, etc. In this way, the classifier may not only provide information related to the gestures to be "found" by the system, but also to other gestures. In this way, the classifier could not only output that the signal was not a "double jaw clenching signal", but the specific action being performed, such as "talking." In this way, resistance to false positives is provided thanks to specific dataset collection of natural head movements that would otherwise have a signature close to a jaw clenching gesture. The raw data and derivatives thereof could include false positive gesture signals that are specific to a particular user. The false positive gesture signals could be mined from a user explicitly (e.g., by providing them with instructions to talk or swallow and tagging the recorded data) or implicitly (e.g., by intuiting the case of detected false negative signals from a microphone detecting the users voice or by identifying false negative signals intuited using other means described above as being similar to similar false negative signals in a library thereof drawn from the general population).

The prediction model described as the sophisticated model (higher-power high accuracy mode) above can aim at detecting jaw clenching gestures with very high precision (i.e., very few false positives) and very high recall (i.e., very few false negatives). In order to do so, a big challenge is to avoid confusion between proper jaw clenching events to be used by the system (whether it is double, triple or long jaw clenching) and every other common gesture performed by the subject. Especially, some gestures are very common and can be performed by the subject quite frequently with no intention to use the system to control the electronic device. Some of these gestures can include the activity of the masseter muscles (for instance chewing, talking, swallowing) which makes them good candidates for false positive detection.

A good strategy to avoid such false positives is to collect as much data as possible of such gestures, to allow the model to learn the (sometimes subtle) differences between those and jaw clenching gestures of interest. In case the model use explicitly engineered features (e.g., rule-based model with thresholds defined on signal amplitude, "classic" Machine Learning models like SVC, Logistic Regression, etc.), those features need to be designed so that they contain sufficient information for the model to differentiate the different gestures (e.g., peak counter, where a double jaw clenching shows two peaks for example in a 2 s time window, whereas chewing shows more peaks, spaced by a regular time interval).

In case the model takes signal windows as an input without requiring any feature engineering beforehand (e.g., Neural Networks), then the model can be able to learn the subtle differences between those gestures during its training phase. Also, the data used to train the model can have a significant impact on the latency between the moment the user performs the jaw clenching gesture and the moment the action is triggered on the electronic device.

Figure 6:
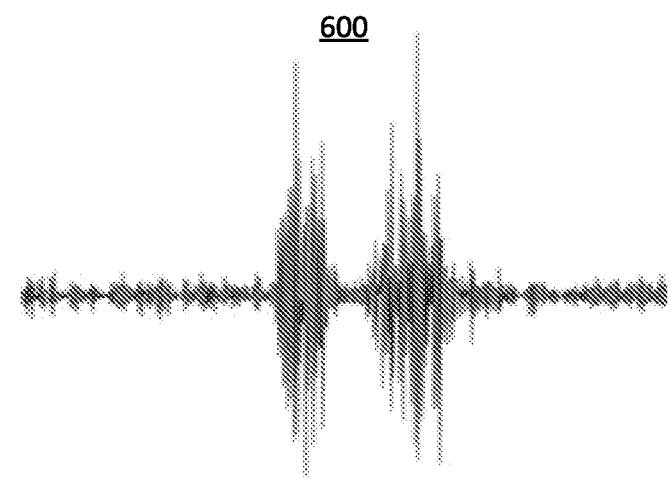
FIG. 6 includes examples of signals as measured by the electrodes in different times and duration, in accordance with specific embodiments of the invention disclosed herein.
Figure 6:
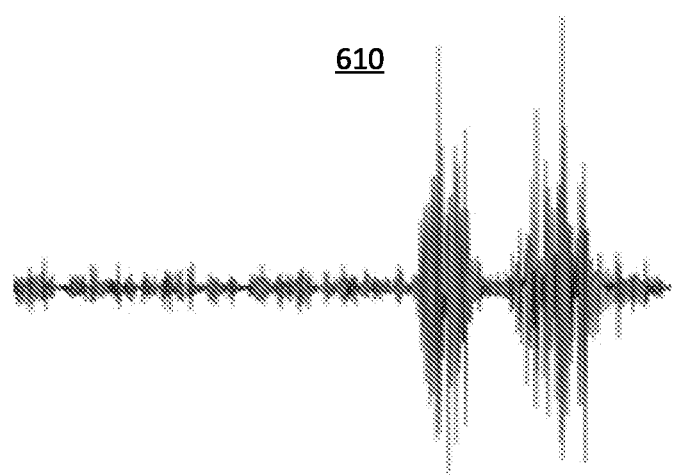
Figure 6:
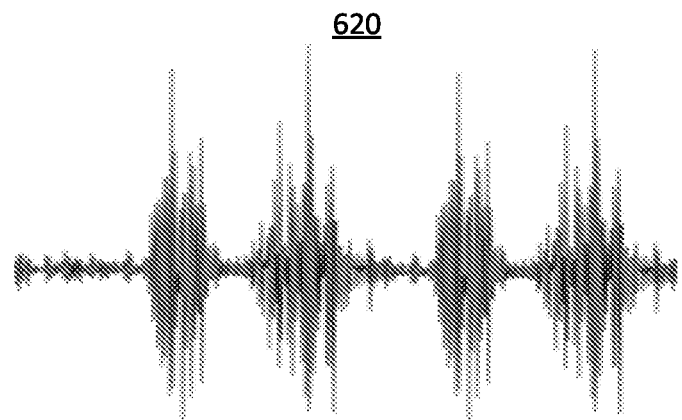

As an example, if the model can be trained using only time windows where the jaw clenching signal is centered (as represented in signal 600 of FIG. 6), then it will most likely be unable to detect a jaw clenching that would appear on a side of the window (for example as represented in signal 610). However, as described before in this disclosure, when data is being recorded continuously, the first time windows to contain a given jaw clenching event can look like the example of signal 610, with the event shifted to the right. In that case, it may be necessary to wait for a few more windows until the jaw clenching event is centered like in signal 600, which may lead to an increase in the latency.

On the other hand, events cannot be simply detected as soon as they appear in the window, because this could increase the chances of confusing it with other events and trigger false positives. For instance, signal 610 could correspond to a subject who just started chewing, and in that case waiting a little longer would help avoid confusion as the input window would look like the one in signal 620.

In specific embodiments of the invention, the system is configured to monitor a contact condition of the electrodes. The system can be configured to generate an alert signal upon detecting that the contact condition of any of the electrode has failed. The alert signal can be a direct indication that the contact condition is poor or was lost, for example an indication on a display, or via a speaker or other means to provide feedback disclosed herein. The alert signal can also be a control command to trigger a certain action within the system, for example stop playing music, end a call, and the like.

EMG signal quality is tied to a consistent contact between the electrodes and the skin. If there is no contact, no EMG signal can be transmitted from the body to the electronics. If the area of contact changes, the impedance of the electrode changes accordingly, which can directly affect the signal measured by creating some electrode-movement artefacts.

Specific embodiments of the invention relate to monitoring the electrodes contact quality, which can be done in several ways. For example, a very low intensity current can be injected through one electrode and the recording from other electrodes can be observed. This can be a standard procedure for measuring the impedance of the electrode-skin interface. If the impedance is too high or varies too much, there is likely a poor contact quality. As another example, the signal measured by the electrode can be observed. If the electrode-skin contact varies a lot (due to significant electrode movement for instance) then the signal will likely display related patterns in the low frequencies (e.g., if the user is walking at a pace of 2 steps per second and the earbuds with embedded electrodes are a little loose, there will likely be a strong signal component at around 2 Hz).

Observing those patterns can be used as an indicator that the contact between the electrodes and the skin is not consistent.

When the electrodes are no longer in touch with the skin, the output signal of the analog amplifier can diverge to one of its extreme values (and possibly alternate). This is sometimes called lead-off detection. Additionally, the numerical signal at the output of the ADC can reach its extreme values (and possibly alternate). This can be used to detect for instance that an earbud has been removed by the subject and activate some commands accordingly (e.g., trigger an alert, pause the music, etc.). Jaw clenching detection can be deactivated if there is a bad contact (for the signal related to the electrode with a bad contact).

Figure 7:
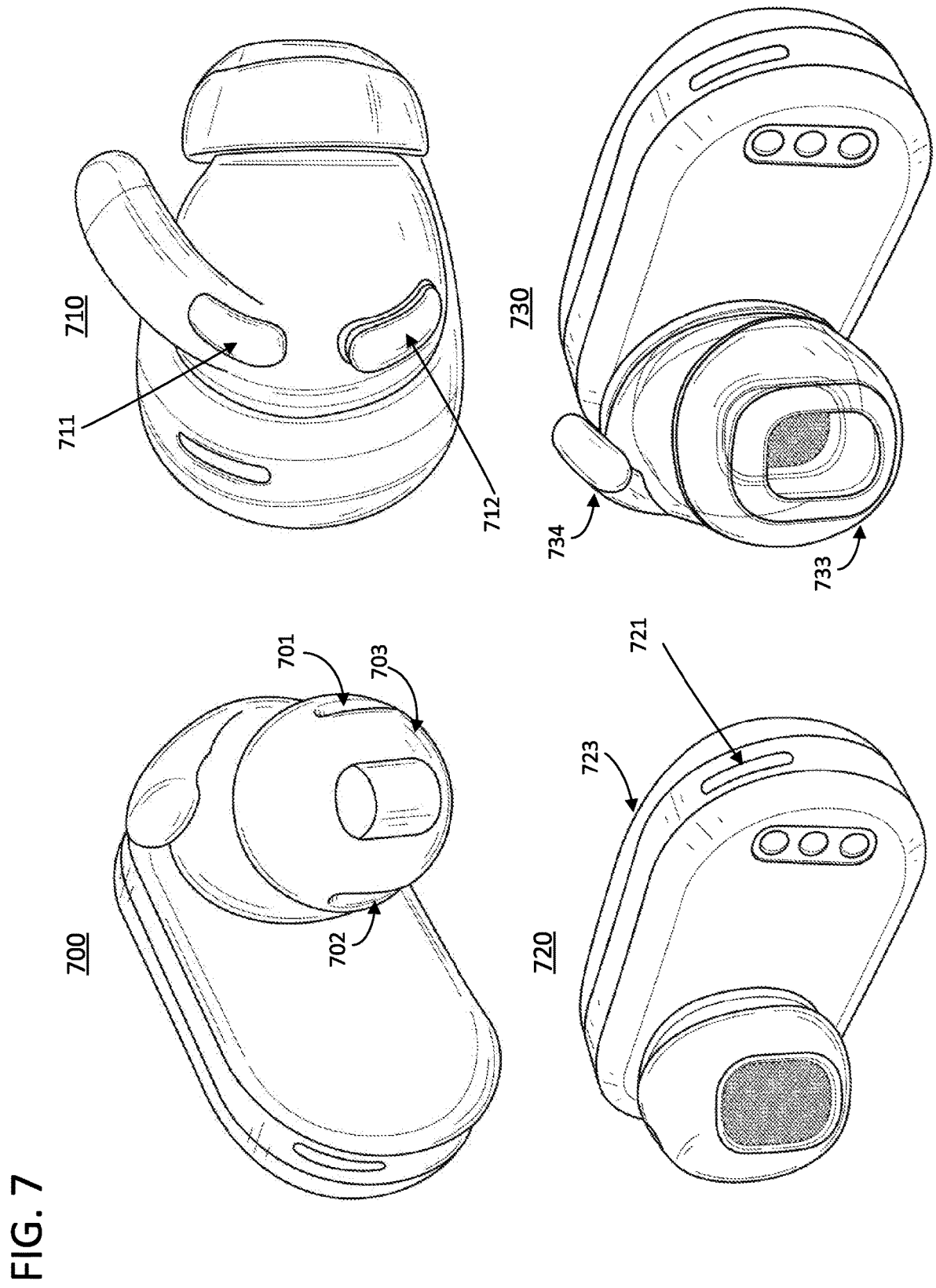
FIG. 7 includes examples of earpieces comprising electrodes at different locations, in accordance with specific embodiments of the invention disclosed herein.

FIG. 7 includes examples of personal head wearable devices in the form of earbuds in accordance with specific embodiments of the invention. The earbud 700 comprises two electrodes 701 and 702 located on an external surface of the earbud. In this example, the electrodes are located on the ear tip 703 of the earbud, which is to be placed in the ear canal when the earbud is worn. In this way, the electrodes will be located in the ear canal when worn.

As described before in this disclosure, the bioelectric signal is measured by measuring the differential voltage between a measurement electrode and a reference electrode. In order to get as good a Signal-to-Noise Ratio (SNR) as possible, it can be advantageous to place the measurement electrode as close as possible to the source of the signal of interest, and the reference electrode at a location that minimizes signal collection from the source, while still being close enough to the measurement electrode so as to capture a noise component as similar as possible to that captured by the measurement electrode. A theoretical ideal setup can involve a measurement electrode recording M=Signal+ Noise, a reference electrode recording R=Noise, and a differential signal D=M−R=Signal. In practice, the noise components captured by the measurement electrode and the reference electrode can be different, and the reference electrode can also capture some signal. In this way, it can be considered a measurement electrode recording M=Signal1+ Noise1, a reference electrode recording R=Signal2+Noise2, and a differential signal D=M−R=(Signal1−Signal2)+ (Noise1−Noise2).

In the specific embodiments of the invention where the electrodes are located in the ear, they can be located in the ear canal, as explained with reference to earbud 700, in the inferior concha, the superior concha, the ear lobe, the tragus, etc., or anywhere else around the ear. In case the system is designed to work in a "single-ear" fashion (each earbud can work independently), both the measurement and the reference electrode are located on the same earbud. This can imply a strong constraint on the distance between measurement and reference electrodes, which are usually placed further apart than an ear-size in common EMG systems.

Hence a key factor to increase SNR for the single-ear setup is to maximize the distance between measurement and reference electrode. Several non-limiting setups to place the electrodes are illustrated in this disclosure. One setup is shown with reference to earbud 700, where both electrodes are placed on the ear tip 703 of the earbud. This setup usually allows a good contact of the electrodes with the skin, since the ear tip maintains some pressure of the electrode on the ear canal, but the electrodes are quite close together.

Another configuration is illustrated for earbuds 710 and 720, where one or both electrodes are located on the housing 723 of the earbud (electrodes 711 and 712 in earbud 710 and electrode 721 in earbud 720). It can be more complicated to ensure a good and sustained contact between the electrodes and the skin with such setup, especially since the size of the housing is usually fixed and may not be possible to customize it to the user's ear shape and size. Hence the contact areas between the housing of the earbud and the ear may vary drastically from one subject to another. However, on the other hand, using the housing to place the electrodes allows to take advantage of the full size of the earbud and maximize the distance between the electrodes (e.g., by placing measurement electrode in position 712 and reference electrode in position 721).

To cope with the imperfections of these solutions, in specific embodiments of the invention parts of the earbuds, such as the ear tip 733 and the ear wing 734, represented for earbud 730, can be used to place the electrodes. In those embodiments, one electrode can be on the ear wing of the earbud and the other electrode is on the ear tip. Soft conductive materials can be used to build ear tips and ear wings that are conductive (at least some part of it). When those parts are made of soft and flexible materials and worn such that they exercise a pressure on the skin of the ear canal (for the ear tip) or the superior concha (for the ear wing), a good and consistent electro-skin contact can be maintained. Those parts of the earbud can come in different sizes (either as a block as shown in earbud 730, or separately), which can allow a certain level of customization for a given subject's ear size and shape, improving the contact quality. Those parts of the earbud can be changeable, meaning they can be replaced when they are worn, and hence don't affect the durability of the whole system. Also, this makes the cleaning of those parts much easier. The ear wing electrode can include one or more gold/conductive electrodes like small plugs, which can come in various sizes and exercises a pressure on the skin so that the electrode-skin contact is guaranteed.

Figure 8:
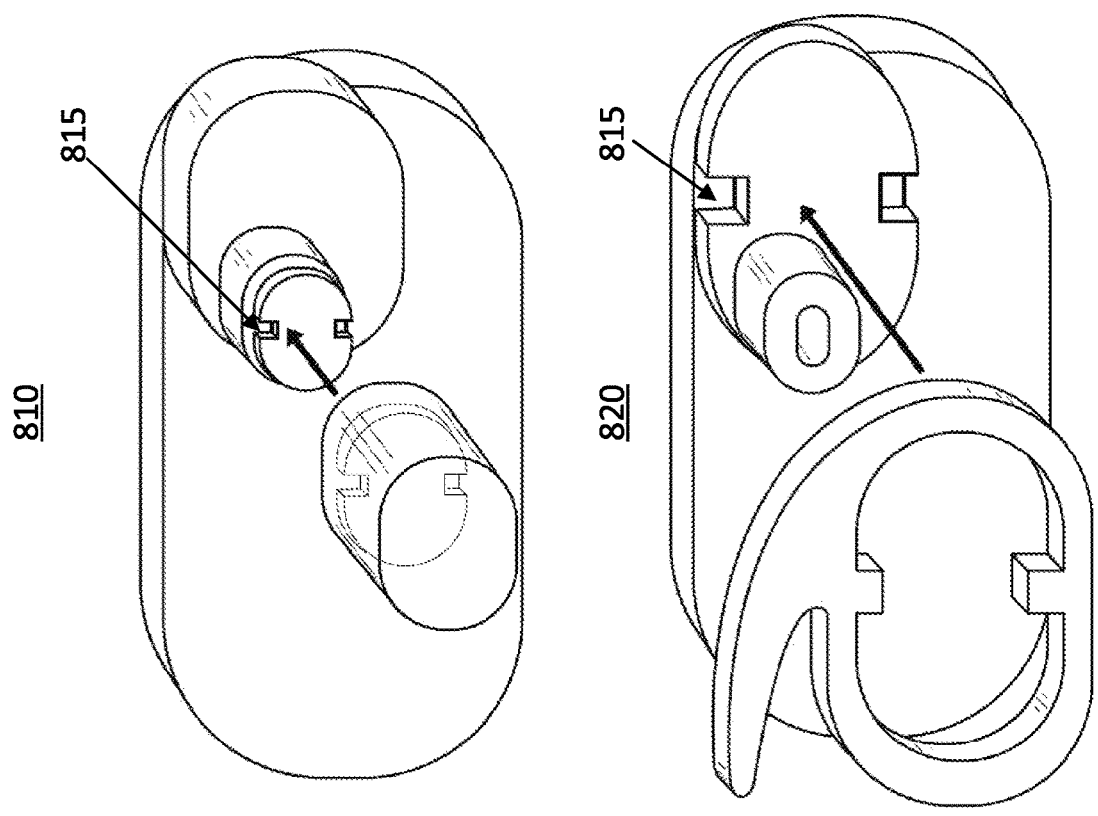
FIG. 8 includes examples of connector configurations, in accordance with specific embodiments of the invention disclosed herein.
Figure 8:
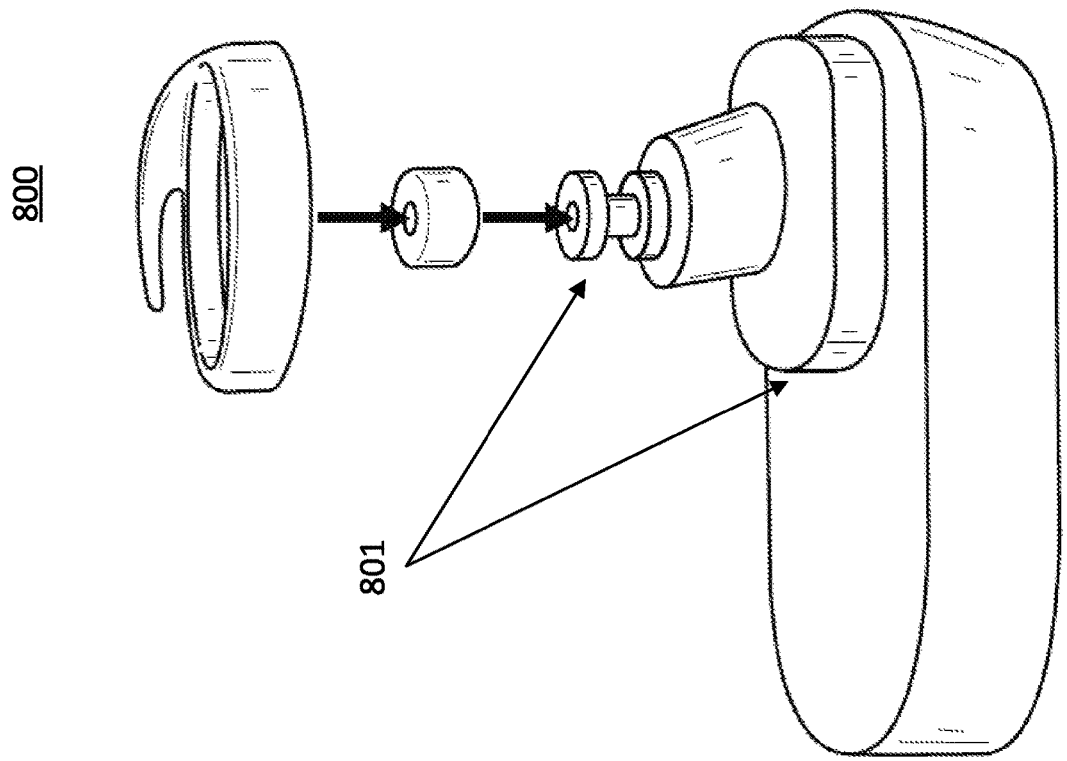

To ensure an electrical connection between the removable soft electrodes and the electronics contained within the housing of the earbud, a system can be used where a conductive element (that can be made of a metal or another conductive material) can be used as a connector. This connector can have a part that emerges on the surface of the housing, and a part that reaches the AFE within the housing, as illustrated in FIG. 8. Illustration 800 shows connectors 801 for the ear wing and ear tip. Illustrations 810 and 820 show variants of connectors for the ear wing and ear tip, with a hook 815 to maintain the ear wing or ear tip in a predefined position.

The material of the electrodes, such as ear tip and ear wing electrodes can be selected from various candidates with certain properties. For example, the material can be a good electronic conductor as well as a good transducer of ionic currents into electronic currents, such that the resulting electrode-skin interface can have an acceptable impedance (for example less than 1 M Ohm for the typical sizes of electrodes considered). Those good conductive properties can be obtained, for example, by using an electroconductive gel between the electrode and the skin, but the usage of such gel may not be appropriate and therefore the materials selected can obtain good conductive properties by building what is called "dry electrodes" using them.

In specific embodiment of the invention, the material of the electrodes can also be water resistant so that sweat won't deteriorate it too fast, and so that the electrodes made out of these materials can be easily cleaned using water, for instance to remove earwax that can build up with normal usage. Additionally, the material can be comfortable enough—on par with existing non-conductive ear tips and ear wings currently integrated in earbuds—so that the user can wear the earbuds for several hours without pain or discomfort.

Candidate materials can include composite polymers, such as silicone (e.g., PDMS, Ecoflex, etc.) mixed with electronic-conductive particles (e.g., carbon black, CNT, graphite, Ag, etc.) and/or ionic-conductive particles (e.g., Ag/AgCl, etc.). Candidate materials can also include intrinsically conductive polymers, which include polymers that have conductive properties due to their original composition (e.g., PEDOT:PSS) mixed with additive to give them water resistant, stretchable or adhesive properties (e.g., waterborne polyurethane—WPU, D-sorbitol). Candidate materials can also include metal-coated fabric (e.g., coating using silver and silver chloride) and other suitable materials. The examples provided herein are not limiting examples of candidate materials.

In specific embodiment of the invention, the electrodes can comprise a surface of composite polymer. The composite polymer can be a rubber polymer mixed with conductive particles. The rubber polymer can be soft silicone. The conductive particles can include at least one of carbon black, carbon nanotubes, graphite, silver and silver chloride. In specific embodiment of the invention, the electrodes comprise an intrinsically conductive polymer. The intrinsically conductive polymer can have a conductive original composition and a water-resistant additive.

As mentioned before in this disclosure, the system in accordance with specific embodiments of the invention can provide different kinds of feedback in different situations. The feedback can be auditory, visual, and/or haptic feedback. A feedback can be provided if the user wants to know whether the measured signal is good enough and the EMG technology can be triggered. A feedback can also be provided if a user wants to get a validation the gesture has been properly recognized and the action tied to it has been performed. Many other non-limiting situations have been disclosed herein where a feedback may be a considerable feature.

In specific embodiments of the invention, the system can provide feedback related to a signal quality detection. For example, one or more feedbacks can be provided indicating that there is a good signal quality or that there is not a good signal quality. This detection can be triggered according to various scenarios. For example, feedback can be provided continuously while the earpiece is worn. In those cases, whenever the contact is detected, the quality of the EMG signal is continuously measured and feedback triggered appropriately.

Feedback can also be provided after specific events occur while the earpiece is worn. It is very likely that the signal quality may not be good enough all the time while the user is wearing the earpiece. However, providing too many feedbacks to the user over time may create some frustration and it may be desirable to limit the moment when the signal quality detection is activated. Feedback can also be provided when the earpiece was not worn a moment before, for example if it is detected that the user is about or has just put the earpiece in their ears, for example when the user removes the earpiece from the case, or when a contact is detected while no contact was detected a moment before, in both cases the signal quality detection can be activated for the next 1-5 minutes.

When the user already received a feedback moments ago but didn't act upon it, no additional feedback may be provided to the user for the next 2-10 minutes. When the user just triggered a gesture, haptic or voice control on the device it may be desirable to activate the signal quality detection for the next 1-5 minutes. This is especially true if the user triggered a haptic/voice control after the system detected a gesture control, as it most likely means this was a false positive potentially detected because of poor signal quality.

Different types of feedback can be provided. For example, an audio feedback can be provided when an earpiece is worn while it was not worn a moment ago. The feedback can be, for example, a standard chime, ping, or any kind of sound if a good signal quality is detected, and silent otherwise. Another kind of audio feedback in this scenario can be a chime, ping, or any kind of sound that is specific to the signal quality. An audio feedback can also be provided while the earpiece is worn, for example via a standard chime, ping, or any kind of sound if the signal quality changes and/or a chime, ping, or any kind of sound that that is specific to the signal quality when the signal quality changes.

Haptic Feedback can also be provided, for example when the earpiece is worn while it was not worn a moment ago, with a standard vibration if a good signal quality is detected, and nothing otherwise, and/or with a vibration is specific to the signal quality (e.g., long vibration is good, short vibration otherwise). Feedback can also be provided while the earpiece is worn, for example with a standard vibration if the signal quality changes and/or with a vibration that is specific to the signal quality (e.g., long vibration is good, short vibration otherwise) if the signal quality changes.

Feedback can also be provided for gesture detection confirmation. It may be desirable to provide the users with feedback when they perform a gesture. This gesture can be detected but the action triggered by the gesture may not have any direct visual, haptic or audio consequences. For instance, if a user performs the gesture to open a communication channel, the user can make sure the channel is properly open before they start talking. The different types of feedback can be an audio feedback, with a chime/ping or any kind of sound that is performed when the gesture is detected by the system, and/or a haptic feedback, with a simple vibration when the gesture is detected by the system.

In specific embodiment of the invention, the system can be implemented so that it follows biocompatibility norms, impermeability norms, or other norms. For example, dust and water resistance can be measured by the IP Code. An earphone sold can showcase a IPXY resistance where X refers to "physical particles resistance" (dust) and Y refers to "liquid particles resistance" (water). Not all earphones have a "dust" or "water" resistance indication.

While the specification has been described in detail with respect to specific embodiments of the invention, it will be appreciated that those skilled in the art, upon attaining an understanding of the foregoing, may readily conceive of alterations to, variations of, and equivalents to these embodiments. For example, although the example of earbuds was used throughout this disclosure, any wearable device, particularly ones in close proximity to the head of the user, could be used instead including glasses, contact lenses, earrings, necklaces, hats, and other wearables. Although many examples were given of a jaw clenching recognition, the concepts disclosed herein are equally applied to recognizing other gestures including hand, arm, and finger motions, eye and eye lid movements, and other gestures. These and other modifications and variations to the present invention may be practiced by those skilled in the art, without departing from the scope of the present invention, which is more particularly set forth in the appended claims.

What is claimed is:

1. A gesture detection system comprising:
an earpiece;
a first electrode on an ear wing of the earpiece;
a second electrode on an ear tip of the earpiece, wherein the first electrode and the second electrode measure a bioelectric signal and generate raw data of the bioelectric signal;
one or more processors; and
one or more non-transitory computer readable media storing instructions which, when executed by the one or more processors, cause the system to:
analyze the bioelectric signal to recognize a gesture signal in the bioelectric signal using a stored signature model for the gesture signal;
generate an interface signal upon recognizing the gesture signal in the bioelectric signal;
detect one of: (i) a connection to the system; and (ii) an idle state of the system; and
transmit, upon the detecting, at least one of: (i) the raw data of the bioelectric signal; and (ii) derivatives of the raw data of the bioelectric signal;
wherein the gesture signal is one of: (i) a double jaw clenching signal; (ii) a triple jaw clenching signal; and (iii) a long jaw clenching signal.

2. The gesture detection system of claim 1, further comprising:
a user interface output;
wherein the one or more non-transitory computer readable media further store instructions which, when executed by the one or more processors, cause the system to:
generate a prompt to perform a gesture associated with the gesture signal; and
update the stored signature model using the gesture signal to generate a revised stored signature model;
wherein the interface signal is output on the user interface output; and
wherein the stored signature model is a default model associated with the gesture.

3. The gesture detection system of claim 1, wherein:
the first electrode and the second electrode are on an exterior surface of the earpiece.

4. The gesture detection system of claim 1, wherein the earpiece is a first earpiece and the system further comprising:
a second earpiece; and
a third electrode and a fourth electrode;
wherein the third electrode and the fourth electrode measure the bioelectric signal;
wherein the first electrode and the second electrode are on an exterior surface of the first earpiece;
wherein the third electrode and the fourth electrode are on an exterior surface of the second earpiece; and
wherein the recognizing of the gesture signal in the bioelectric signal uses a combination of: (i) first data measured by the first electrode and the second electrode; and (ii) second data measured by the third electrode and the fourth electrode.

5. The gesture detection system of claim 4, wherein the one or more non-transitory computer readable media store instructions which, when executed by the one or more processors, cause the system to:
determine if the bioelectric signal is present in the first data and the second data;
wherein the recognizing of the gesture signal in the bioelectric signal uses the combination and the stored signature model if the bioelectric signal is present in both the first data and the second data; and
wherein the recognizing of the gesture signal in the bioelectric signal uses only one of the first data and the second data, and the stored signature model if the bioelectric signal is present in only one of the first data and the second data.

6. The gesture detection system of claim 1, wherein:
the recognizing of the gesture signal in the bioelectric signal uses a combination of first data measured by the first electrode and second data measured by the second electrode; and
the system is configured to:
determine a common mode signal of the first data and the second data; and
feedback an opposite of the common mode signal to cancel the common mode signal.

7. The gesture detection system of claim 1, wherein the earpiece is a first earpiece and the system further comprising:
a second earpiece, wired to the first earpiece; and
a third electrode and a fourth electrode on an exterior surface of the second earpiece;
wherein the recognizing of the gesture signal in the bioelectric signal uses a combination of: (i) data measured by the first electrode and the fourth electrode; and (ii) data measured by the third electrode and the second electrode.

8. The gesture detection system of claim 1, wherein the earpiece is a first earpiece and the system further comprising:
a third electrode on an exterior surface of the first earpiece;
a second earpiece; and
a fourth electrode, a fifth electrode, and a sixth electrode on an exterior surface of the second earpiece;
wherein the recognizing of the gesture signal in the bioelectric signal uses a combination of: (i) data measured by the first electrode and the second electrode using the third electrode as a first reference electrode; and (ii) data measured by the fourth electrode and the fifth electrode using the sixth electrode as a second reference electrode.

9. The gesture detection system of claim 1, wherein the one or more non-transitory computer readable media store instructions which, when executed by the one or more processors, cause the system to:
sample the bioelectric signal using a sliding window; and
perform the recognizing of the gesture signal in the bioelectric signal using data from the sliding window;
wherein the sliding window has a period of one to three seconds; and
wherein the sliding window has a sample interval from 0.1 to 0.5 seconds.

10. The gesture detection system of claim 1, wherein the one or more non-transitory computer readable media store instructions which, when executed by the one or more processors, cause the system to:
determine an average power of the bioelectric signal when no gesture signal is recognized; and
normalize the bioelectric signal using the determined average power.

11. The gesture detection system of claim 1, wherein the one or more non-transitory computer readable media store instructions which, when executed by the one or more processors, cause the system to:

operate in a low-power high sensitivity mode;
detect a potential gesture signal in the low power high sensitivity mode; and
trigger a higher-power high accuracy mode upon detecting the potential gesture signal.

12. The gesture detection system of claim 1, further comprising:
a filter for filtering the bioelectric signal as measured by the first electrode and the second electrode;
wherein the filter includes at least a high pass filter response; and
wherein the high pass filter response has a cutoff frequency between 50 hertz and 90 hertz.

13. The gesture detection system of claim 1, further comprising:
a filter for filtering the bioelectric signal as measured by the first electrode and the second electrode;
wherein the filter is configured to reject at least one of: 100 hertz; 120 hertz; and 100 hertz and 120 hertz.

14. The gesture detection system of claim 1, wherein:
the one or more non-transitory computer readable media store instructions which, when executed by the one or more processors, cause the system to sample the bioelectric signal as measured by the first electrode and the second electrode using a sample frequency; and
the sample frequency is between 125 hertz and 500 hertz.

15. The gesture detection system of claim 1, wherein:
the stored signature model is a classifier;
a set of false positive gesture signals are embedded in the classifier; and
the set of false positive gesture signals includes at least one of: (i) a chewing signal; (ii) a talking signal; (iii) a swallowing signal; (iv) a lateral head movement signal.

16. The gesture detection system of claim 1, wherein the one or more non-transitory computer readable media further store instructions which, when executed by the one or more processors, cause the system to:
monitor a contact condition of the first electrode and the second electrode; and
generate an alert signal upon detecting that the contact condition of the first electrode or the second electrode has failed.

17. The gesture detection system of claim 1, wherein:
the first electrode and the second electrode comprise a surface of composite polymer configured for skin contact; and
the composite polymer is a rubber polymer mixed with conductive particles.

18. The gesture detection system of claim 17, wherein:
the rubber polymer is soft silicone; and
the conductive particles include at least one of: carbon black, carbon nanotubes, graphite, silver and silver chloride.

19. The gesture detection system of claim 1, wherein:
the first electrode and the second electrode comprise an intrinsically conductive polymer; and
the intrinsically conductive polymer has a conductive original composition and a water resistant additive.

20. The gesture detection system of claim 1, further comprising:
a speaker;
wherein the one or more non-transitory computer readable media further store instructions which, when executed by the one or more processors, cause the system to generate an auditory feedback signal to be rendered by the speaker upon generation of the interface signal.

21. A wearable gesture recognition system comprising:
a first earpiece;
a first electrode and a second electrode, wherein the first electrode and the second electrode are on an exterior surface of the first earpiece, and wherein the first electrode and the second electrode measure a bioelectric signal;
a second earpiece;
a third electrode and a fourth electrode, wherein the third electrode and the fourth electrode are on an exterior surface of the second earpiece, and wherein the third electrode and the fourth electrode measure the bioelectric signal;
one or more processors; and
one or more non-transitory computer readable media storing instructions which, when executed by the one or more processors, cause the system to:
determine if the bioelectric signal is present in (i) first data measured by the first electrode and the second electrode and (ii) second data measured by the third electrode and the fourth electrode;
analyze the bioelectric signal to recognize a gesture signal in the bioelectric signal; and
generate an interface signal upon recognizing the gesture signal in the bioelectric signal;
wherein the recognizing of the gesture signal in the bioelectric signal uses a combination of: (i) the first data; and (ii) the second data and a stored signature model if the bioelectric signal is present in both the first data and the second data;
wherein the recognizing of the gesture signal in the bioelectric signal uses only one of the first data and the second data, and the stored signature model if the bioelectric signal is present in only one of the first data and the second data; and
wherein the gesture signal is one of: (i) a double jaw clenching signal; (ii) a triple jaw clenching signal; and (iii) a long jaw clenching signal.

22. The wearable gesture recognition system of claim 21, further comprising:
a fifth electrode on an exterior surface of the first earpiece; and
a sixth electrode on an exterior surface of the second earpiece;
wherein the recognizing of the gesture signal in the bioelectric signal uses a combination of: (i) data measured by the first electrode and the second electrode using the fifth electrode as a first reference electrode; and (ii) data measured by the third electrode and the fourth electrode using the sixth electrode as a second reference electrode.

23. The wearable gesture recognition system of claim 21, further comprising:
a user interface output;
wherein the one or more non-transitory computer readable media store instructions which, when executed by the one or more processors, cause the system to:
generate a prompt to perform a gesture associated with the gesture signal; and
update the stored signature model using the gesture signal to generate a revised stored signature model;
wherein the interface signal is output on the user interface output; and
wherein the stored signature model is a default signature model associated with the gesture.

24. A gesture detection method for a personal head wearable device comprising the steps of:
   measuring a bioelectric signal using a first electrode and a second electrode, wherein the personal head wearable device includes an earpiece, the first electrode is located on an ear wing of the earpiece, and the second electrode is located on an ear tip of the earpiece;
   analyzing the bioelectric signal to recognize a gesture signal in the bioelectric signal using a stored signature model for the gesture signal and a combination of first data measured by the first electrode and second data measured by the second electrode;
   determining a common mode signal of the first data and the second data; and
   feeding back an opposite of the common mode signal to cancel the common mode signal;
   generating an interface signal upon recognizing the gesture signal in the bioelectric signal;
   wherein the gesture signal is one of: (i) a double jaw clenching signal; (ii) a triple jaw clenching signal; and (iii) a long jaw clenching signal.

25. A gesture detection system comprising:
   a first earpiece;
   a first electrode on an ear wing of the first earpiece;
   a second electrode on an ear tip of the first earpiece, wherein the first electrode and the second electrode measure a bioelectric signal;
   a second earpiece wired to the first earpiece;
   a third electrode and a fourth electrode on an exterior surface of the second earpiece;
   one or more processors; and
   one or more non-transitory computer readable media storing instructions which, when executed by the one or more processors, cause the system to:
      analyze the bioelectric signal to recognize a gesture signal in the bioelectric signal using a stored signature model for the gesture signal; and
      generate an interface signal upon recognizing the gesture signal in the bioelectric signal;
   wherein the recognizing of the gesture signal in the bioelectric signal uses a combination of: (i) data measured by the first electrode and the fourth electrode; and (ii) data measured by the third electrode and the second electrode; and
   wherein the gesture signal is one of: (i) a double jaw clenching signal; (ii) a triple jaw clenching signal; and (iii) a long jaw clenching signal.

26. A gesture detection system comprising:
   an earpiece;
   a first electrode on an ear wing of the earpiece;
   a second electrode on an ear tip of the earpiece, wherein the first electrode and the second electrode measure a bioelectric signal;
   one or more processors; and
   one or more non-transitory computer readable media storing instructions which, when executed by the one or more processors, cause the system to:
      sample the bioelectric signal using a sliding window;
      analyze the bioelectric signal to recognize a gesture signal in the bioelectric signal using a stored signature model for the gesture signal and using data from the sliding window; and
      generate an interface signal upon recognizing the gesture signal in the bioelectric signal;
   wherein the sliding window has a period of one to three seconds;
   wherein the sliding window has a sample interval from 0.1 to 0.5 seconds; and
   wherein the gesture signal is one of: (i) a double jaw clenching signal; (ii) a triple jaw clenching signal; and (iii) a long jaw clenching signal.

27. A gesture detection system comprising:
   an earpiece;
   a first electrode on an ear wing of the earpiece;
   a second electrode on an ear tip of the earpiece, wherein the first electrode and the second electrode measure a bioelectric signal;
   one or more processors; and
   one or more non-transitory computer readable media storing instructions which, when executed by the one or more processors, cause the system to:
      analyze the bioelectric signal to recognize a gesture signal in the bioelectric signal using a stored signature model for the gesture signal;
      generate an interface signal upon recognizing the gesture signal in the bioelectric signal;
      determine an average power of the bioelectric signal when no gesture signal is recognized; and
      normalize the bioelectric signal using the determined average power;
   wherein the gesture signal is one of: (i) a double jaw clenching signal; (ii) a triple jaw clenching signal; and (iii) a long jaw clenching signal.

28. A gesture detection system comprising:
   an earpiece;
   a first electrode on an ear wing of the earpiece;
   a second electrode on an ear tip of the earpiece, wherein the first electrode and the second electrode measure a bioelectric signal;
   one or more processors; and
   one or more non-transitory computer readable media storing instructions which, when executed by the one or more processors, cause the system to:
      operate in a low-power high sensitivity mode;
      detect a potential gesture signal in the low power high sensitivity mode;
      trigger a higher-power high accuracy mode upon detecting the potential gesture signal;
      analyze the bioelectric signal to recognize a gesture signal in the bioelectric signal using a stored signature model for the gesture signal; and
      generate an interface signal upon recognizing the gesture signal in the bioelectric signal;
   wherein the gesture signal is one of: (i) a double jaw clenching signal; (ii) a triple jaw clenching signal; and (iii) a long jaw clenching signal.

29. A gesture detection system comprising:
   an earpiece;
   a first electrode on an ear wing of the earpiece;
   a second electrode on an ear tip of the earpiece, wherein the first electrode and the second electrode measure a bioelectric signal;
   one or more processors; and
   one or more non-transitory computer readable media storing instructions which, when executed by the one or more processors, cause the system to:
      analyze the bioelectric signal to recognize a gesture signal in the bioelectric signal using a stored signature model for the gesture signal; and
      generate an interface signal upon recognizing the gesture signal in the bioelectric signal;

wherein the stored signature model is a classifier;
wherein a set of false positive gesture signals are embedded in the classifier;
wherein the set of false positive gesture signals includes at least one of: (i) a chewing signal; (ii) a talking signal; (iii) a swallowing signal; (iv) a lateral head movement signal; and
wherein the gesture signal is one of: (i) a double jaw clenching signal; (ii) a triple jaw clenching signal; and (iii) a long jaw clenching signal.

30. A gesture detection system comprising:
an earpiece;
a first electrode on an ear wing of the earpiece;
a second electrode on an ear tip of the earpiece, wherein the first electrode and the second electrode measure a bioelectric signal;
one or more processors; and
one or more non-transitory computer readable media storing instructions which, when executed by the one or more processors, cause the system to:
  analyze the bioelectric signal to recognize a gesture signal in the bioelectric signal using a stored signature model for the gesture signal; and
  generate an interface signal upon recognizing the gesture signal in the bioelectric signal;
wherein the first electrode and the second electrode comprise an intrinsically conductive polymer;
wherein the intrinsically conductive polymer has a conductive original composition and a water resistant additive; and
wherein the gesture signal is one of: (i) a double jaw clenching signal; (ii) a triple jaw clenching signal; and (iii) a long jaw clenching signal.

31. A gesture detection method, for a personal head wearable device comprising an earpiece, comprising the steps of:
measuring a bioelectric signal using a first electrode on an ear wing of the earpiece and a second electrode on an ear tip of the earpiece, wherein the first electrode and the second electrode measure the bioelectric signal and generate raw data of the bioelectric signal;
analyzing the bioelectric signal to recognize a gesture signal in the bioelectric signal using a stored signature model for the gesture signal;
generating an interface signal upon recognizing the gesture signal in the bioelectric signal;
detecting one of: (i) a connection to the system; and (ii) an idle state of the system; and
transmitting, upon the detecting, at least one of: (i) the raw data of the bioelectric signal; and (ii) derivatives of the raw data of the bioelectric signal;
wherein the gesture signal is one of: (i) a double jaw clenching signal; (ii) a triple jaw clenching signal; and (iii) a long jaw clenching signal.

* * * * *